(12) United States Patent
Bartlett

(10) Patent No.: US 7,828,856 B2
(45) Date of Patent: Nov. 9, 2010

(54) LEG PROSTHESIS SYSTEM AND METHOD

(76) Inventor: Brian Bartlett, 8615 8th St. SE., Everett, WA (US) 98205

( * ) Notice: Subject to any disclaimer, the term of this patent is extended or adjusted under 35 U.S.C. 154(b) by 51 days.

(21) Appl. No.: 11/241,831

(22) Filed: Sep. 30, 2005

(65) Prior Publication Data

US 2006/0167546 A1 Jul. 27, 2006

Related U.S. Application Data

(60) Provisional application No. 60/614,859, filed on Sep. 30, 2004.

(51) Int. Cl.
*A61F 2/68* (2006.01)
(52) U.S. Cl. ...................................................... 623/46
(58) Field of Classification Search .............. 623/39–46
See application file for complete search history.

(56) References Cited

U.S. PATENT DOCUMENTS

| | | | | |
|---|---|---|---|---|
| 173,872 A | * | 2/1876 | Warner | 623/44 |
| 708,685 A | * | 9/1902 | White | 623/37 |
| 5,016,621 A | * | 5/1991 | Bender | 602/26 |
| 5,020,790 A | * | 6/1991 | Beard et al. | 482/4 |
| 7,288,118 B1 | * | 10/2007 | Swanson, Sr. | 623/46 |
| 2003/0153853 A1 | * | 8/2003 | Houser | 602/16 |

* cited by examiner

*Primary Examiner*—Bruce E Snow
(74) *Attorney, Agent, or Firm*—Charles J. Rupnick, Attorney at Law

(57) ABSTRACT

A prosthesis system can have an advantageous use over conventional prostheses in certain activities, including, but not limited to certain sports activities: The system includes, elastic member(s) that can store and release energy. The storing and releasing of energy in the elastic members happens during the movements made by the user and with the application of the user's own body weight while performing an activity. Implementations can also include a variety of routing configurations for the elastic member(s), as well as a variety of mounting points to integrate the elastic member(s) into the system, and/or a variety of adjustable anti-hyperextension members, and/or a variety of interchangeable shoes used for applicable activities.

18 Claims, 29 Drawing Sheets

LEG PROSTHESIS SYSTEM AND METHOD

BACKGROUND OF THE INVENTION

1. Field of the Invention

The present invention is directed generally to prosthesis systems.

2. Description of the Related Art

Conventional prosthesis systems can be difficult to use for various activities including some involving certain sports.

DETAILED DESCRIPTION OF THE INVENTION

Figure 1:
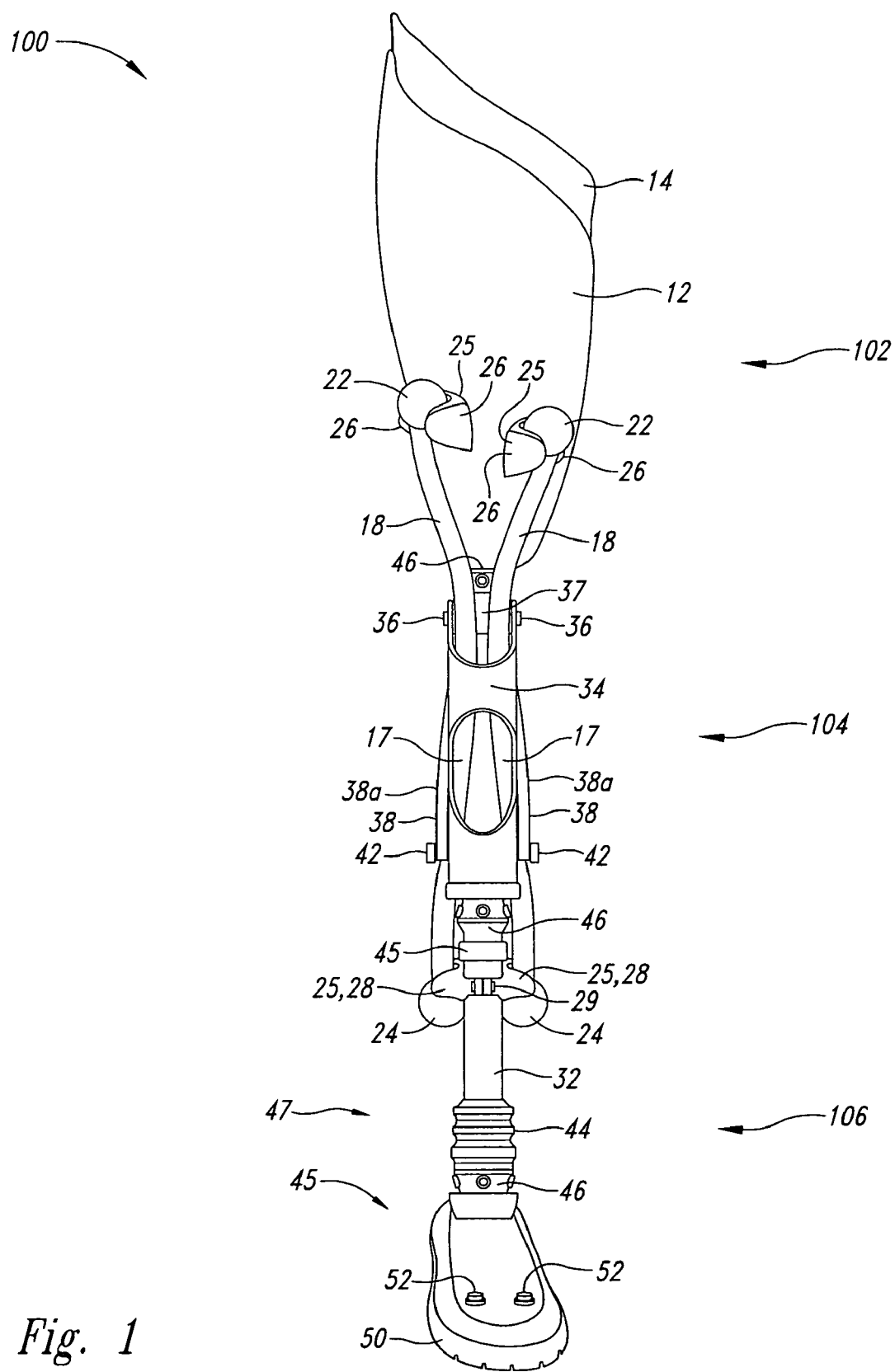
FIG. 1 is a front elevational view of an implementation of a prosthesis system shown in the resting position, having two elastic members routed through the knee frame, and shown with an adjustable strap acting as an anti-hyperextension member.
Figures 2, 3:
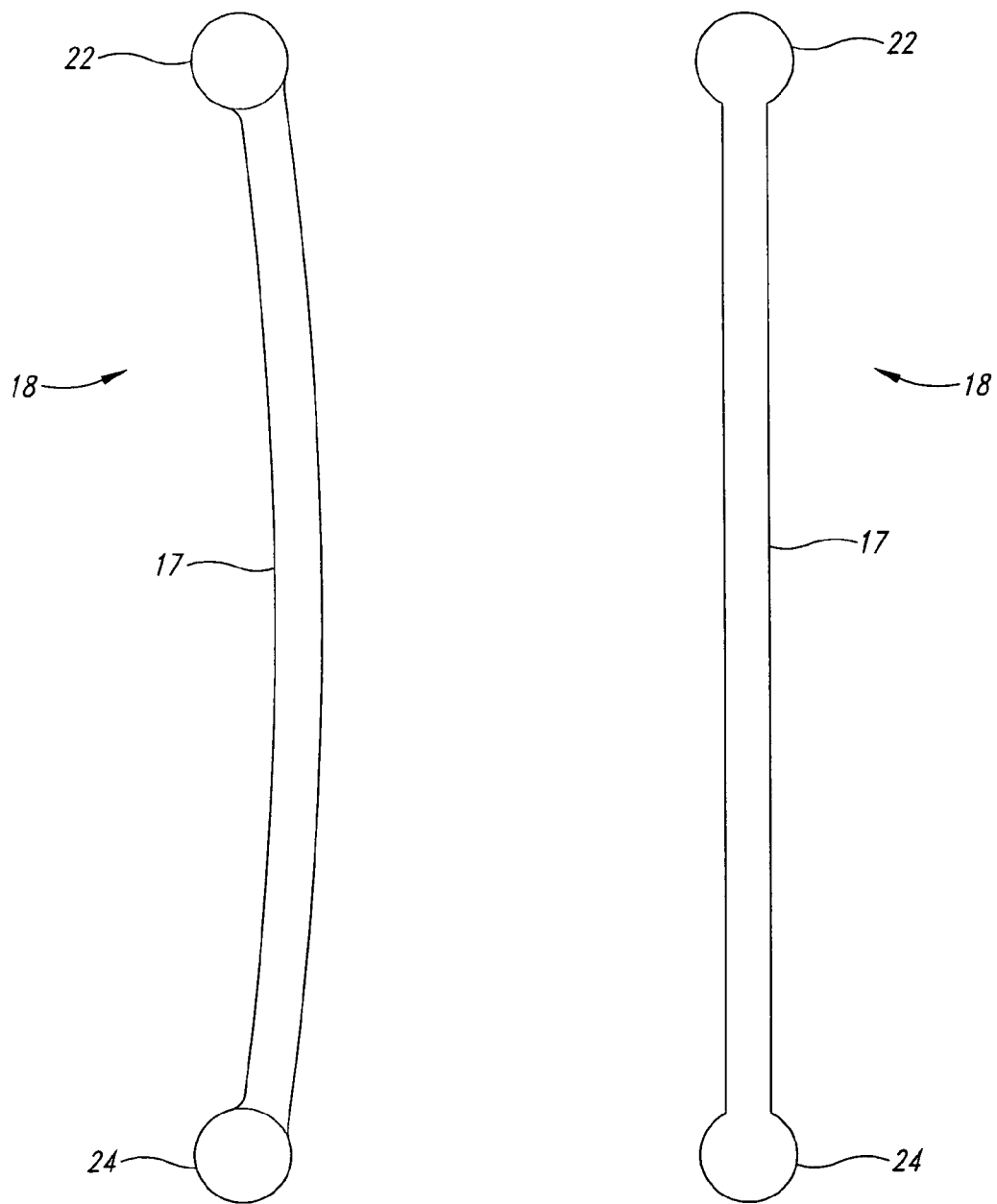
FIG. 2 is a side elevational view of an elastic member.
FIG. 3 is a front elevational view of the elastic member depicted in FIG. 2.
Figure 4:
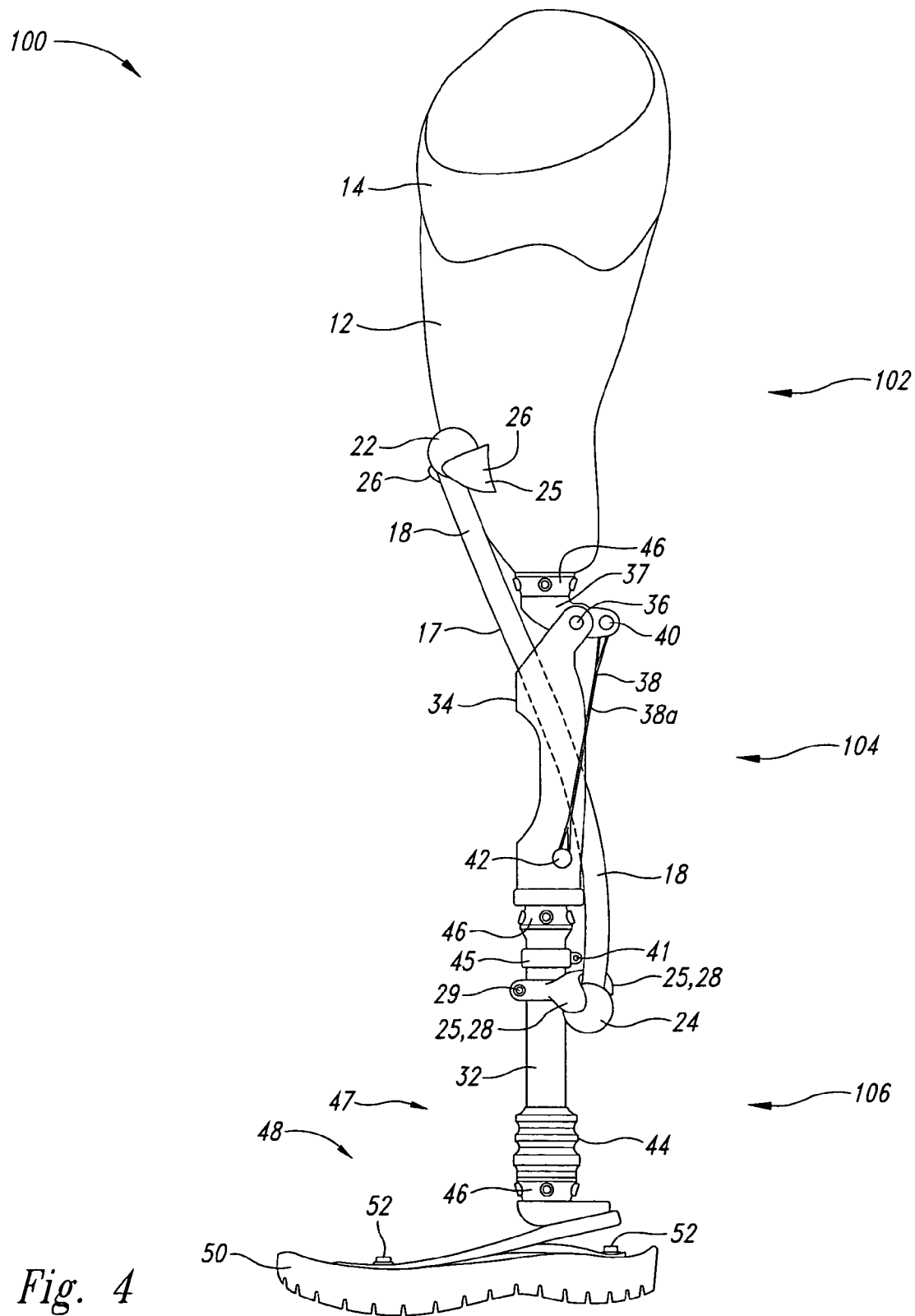
FIG. 4 is a left elevational view of an implementation of the prosthesis system depicted in FIG. 1.
Figure 5:
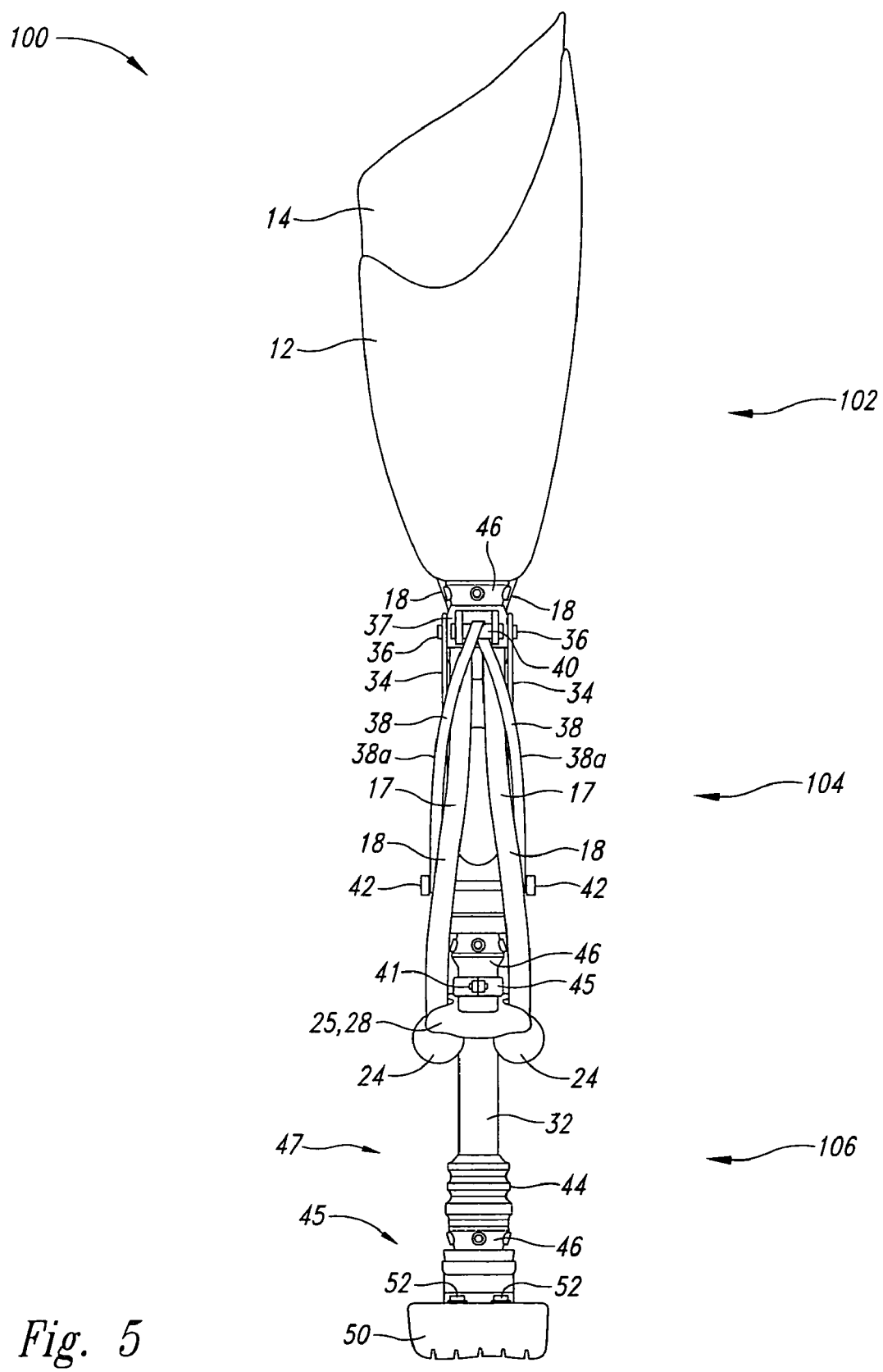
FIG. 5 is a rear elevational view of an implementation of the prosthesis system depicted in FIG. 1.

A prosthesis system described herein allows for energy to be stored and released via one or more elastic member(s). Based upon this approach potential exists for performance advantages over a conventional prosthesis, such as when used in activities requiring the use muscles such as extensor muscles, for instance, the quadriceps. Present implementations can have an advantageous use over conventional prostheses in many activities, including, but not limited to sports activities such as bicycling, surfing, wakeboarding, snowboarding, downhill skiing, cross country skiing, and waterskiing. The system includes, elastic member(s) that can store and release energy. The storing and releasing of energy in the elastic members happens during the movements made by the user and with the application of the user's own body weight while performing an activity. Implementations can also include a variety routing configurations for the elastic member(s), as well as a variety of mounting points to integrate the elastic member(s) into the system, and/or a variety of adjustable anti-hyperextension members, and/or a variety of interchangeable shoes used for applicable activities.

Represented herein is a prosthesis system 100 comprised of an upper portion 102, a joint portion 104, and a lower portion 106. Further included in the system is one or more elastic member(s) 18 for storing and releasing energy, an adjustable anti-hyperextension member 38 that prevents the elastic members 18 from hyper extending the system, a resilient ankle joint 44 in the ankle segment 47 that allows for three-dimensional movement of the foot 48 relative to the lower portion 106, and/or a foot 48 in which the shoe 50 may be changed accordingly to accommodate any various activities the user may wish to engage in.

The implementations shown herein are representing a right leg. A left leg would simply be a mirror image of the right leg, and would incorporate all of the same components, forces, and workings of the right leg. Alternately, all of these same components, forces, and/or workings could also be applied to an elbow, a wrist, a shoulder, and/or an ankle.

Figure 6:
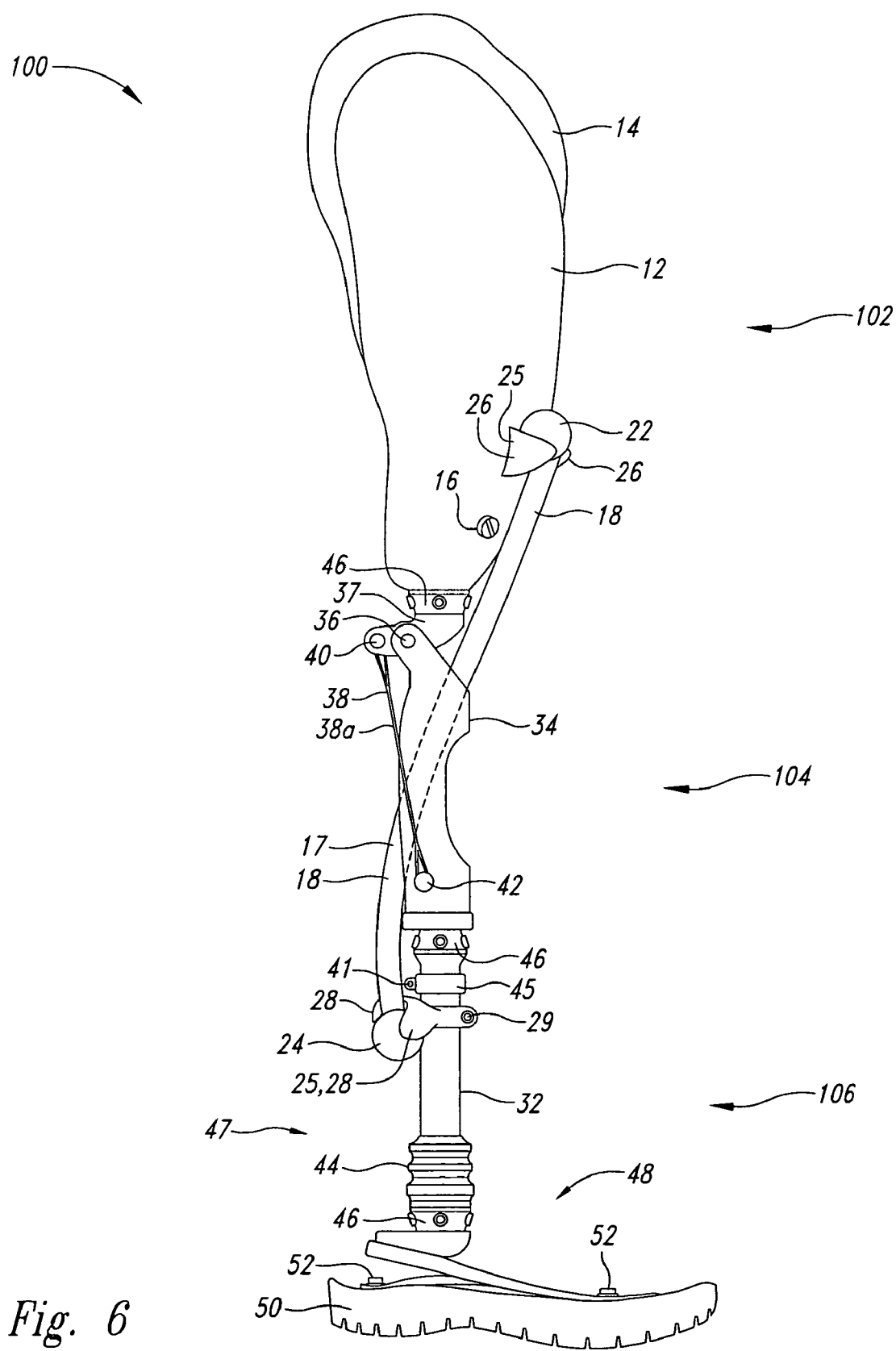
FIG. 6 is a right elevational view of an implementation of the prosthesis system depicted in FIG. 1.

The upper portion 102, used for coupling of the system 100 to the user's leg, may be comprised of an outer socket 12, an inner socket 14, and/or a shuttle lock 16, such as shown in FIG. 6. Further included in the upper portion may be one or more elastic member retainer(s) 25 and 27, such as shown in FIG. 1.

The joint portion 104 of the system 100 may be comprised of one or more pyramid adapter(s) 46, a knee joint 37, a knee frame 34, a knee fulcrum 36, an adjustable anti-hyperextension member 38, an upper attachment point 40, and/or a lower attachment point 42, such as shown in FIG. 6.

The lower portion 106 of the system 100 may be comprised of a coupler 45 for coupling the middle portion 104 to the lower portion 106, a coupler clamp 41, one or more elastic member retainer(s) 25 and 28, a pylon 32, an ankle segment 47, and/or a foot 48. The ankle segment 47 may further encompass a pyramid adapter 46 and/or a resilient ankle joint 44. The resilient ankle joint, allowing a three-dimensional movement of the foot 48 relative to the lower portion 106, will deter any torsional and/or lateral forces being transferred from the foot to the user. This can help alleviate stress on the user's body, and may reduce the potential for injury to the user. The foot 48 may be comprised of a shoe 50 and/or any number of shoe fastener(s) 52. Additionally, the shoe 50 may be removed from the foot 48 via the fastener(s) 52, providing the ability to change the shoe in order to suit any number of various activities such as bicycling, skiing, surfing, snowboarding, and so forth.

Additionally, incorporated into the system 100 is one or more elastic members 18. The elastic member(s) are composed of a resilient material having a middle portion 17 with a decided level of elasticity for storing and releasing energy. The user chooses an elastic member 18 based on it's level of elasticity, the activity for which it will be used in, and according to his or her body weight. It should be noted that a higher level of elasticity would store and release more energy than a lower level of elasticity. The overall length and level of elasticity of the elastic member 18 determines the preloaded tension on the system. Further adjusting of the preload tension of the elastic member(s) 18 can be derived by positioning the lower ball retainer 28 along the longitudinal axis of the pylon 32, via a retainer adjusting element 29.

On opposing longitudinal ends of the elastic member 18 are an upper retaining ball 22 and a lower retaining ball 24, both of which may be comprised of a harder material than the middle portion 17, thereby hindering deformation of the retaining balls 22 and 24 while being retained in the ball retainers 25. Mounting of the elastic member(s) 18 to the system is accomplished via an upper ball retainer 26 and a lower ball retainer 28 located on the upper portion 102 and lower portion 106, respectively, which accept the retaining balls 22 and 24, respectively. Furthermore, alternative mounting locations of the retaining balls 22 and 24 can be derived by determining the locations of the ball retainers 25. The retaining balls 22 and 24 stay secured in the ball retainers 25 through the existing preload tension of the elastic member 18.

Routing of the elastic member(s) 18 can take the form of various configurations described herein.

Two or more elastic members 18 may be mounted to the lower portion 106 via lower ball retainers 28, having the middle portions 17 routed through the knee frame 34 of the joint portion 104, and mounted to the upper portion 102 via upper ball retainers 26, such as shown in FIG. 1.

Figure 9:
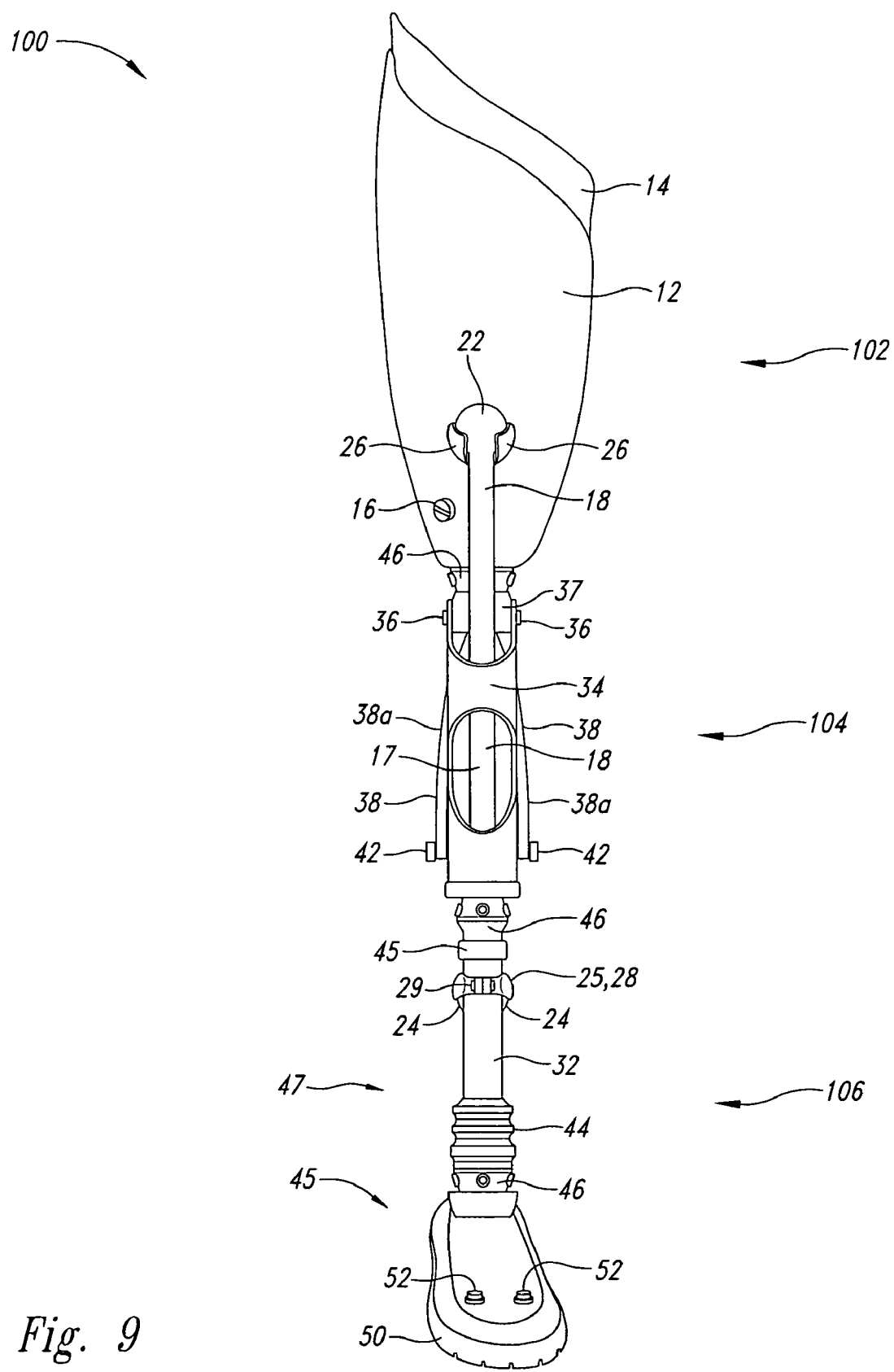
FIG. 9 is a front elevational view of an alternative implementation of a prosthesis system shown in the resting position, having one elastic member routed through the knee frame, and shown with an adjustable strap acting as an anti-hyperextension member.
Figure 10:
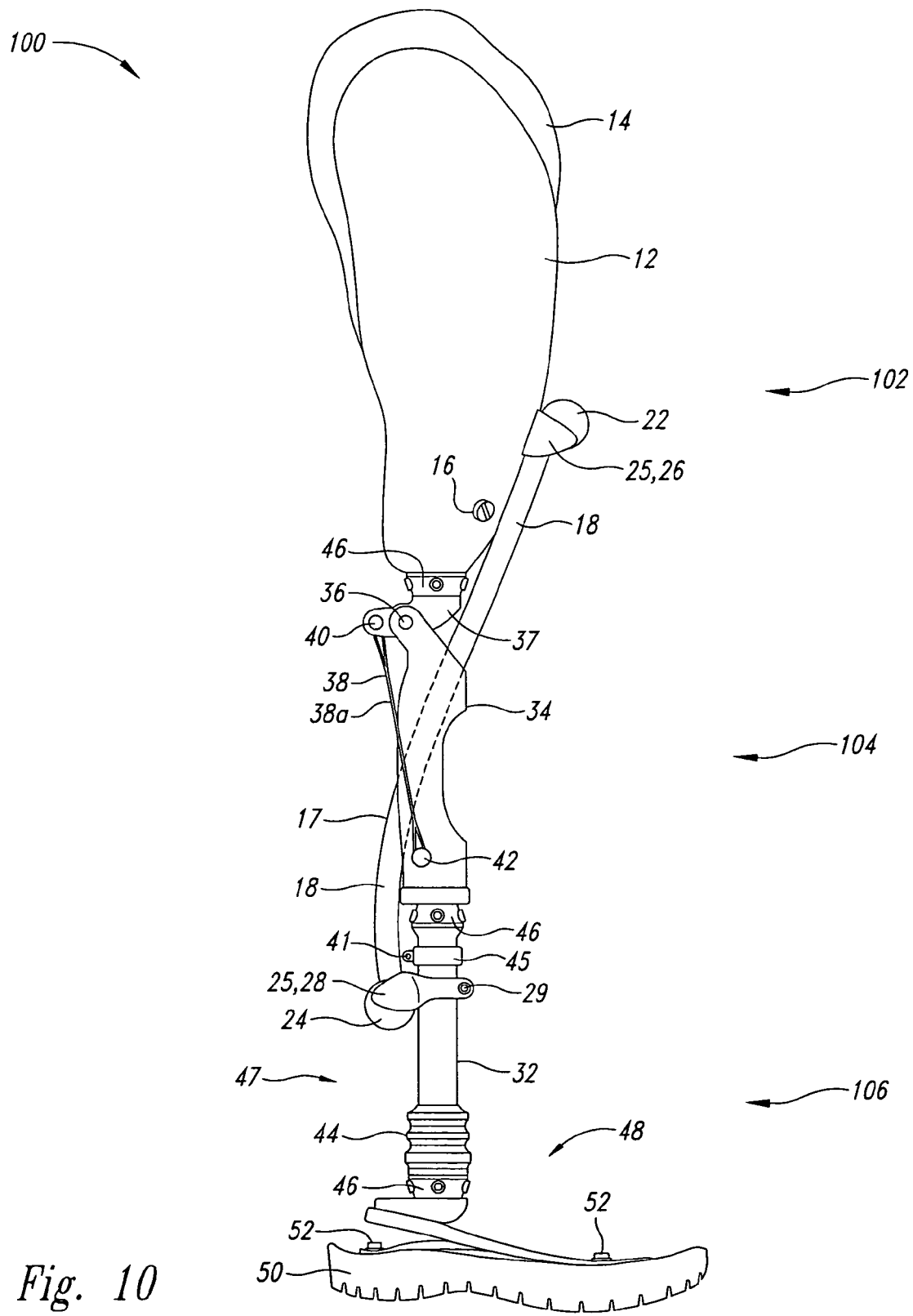
FIG. 10 is a right elevational view of an implementation of the prosthesis system depicted in FIG. 9.

One elastic member 18 may be mounted to the lower portion 106 via a lower ball retainer 28, having the middle portion 17 routed through the knee frame 34 of the joint portion 104, and mounted to the upper portion 102 via an upper ball retainer 26, such as shown in FIG. 9.

Figure 11:
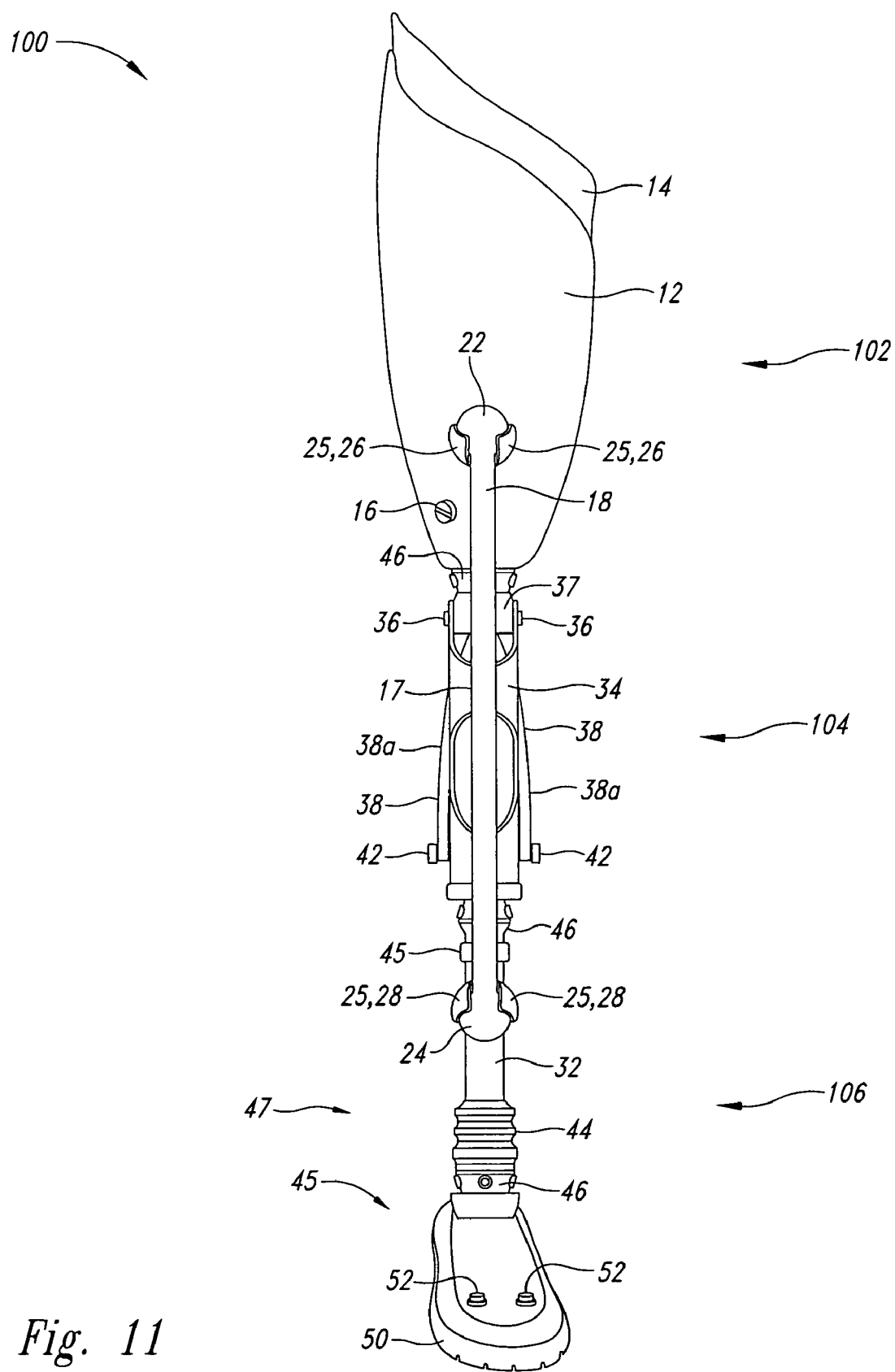
FIG. 11 is a front elevational view of an alternative implementation of a prosthesis system shown in the resting position, having one elastic member frontally routed, and shown with an adjustable strap acting as an anti-hyperextension member.
Figure 12:
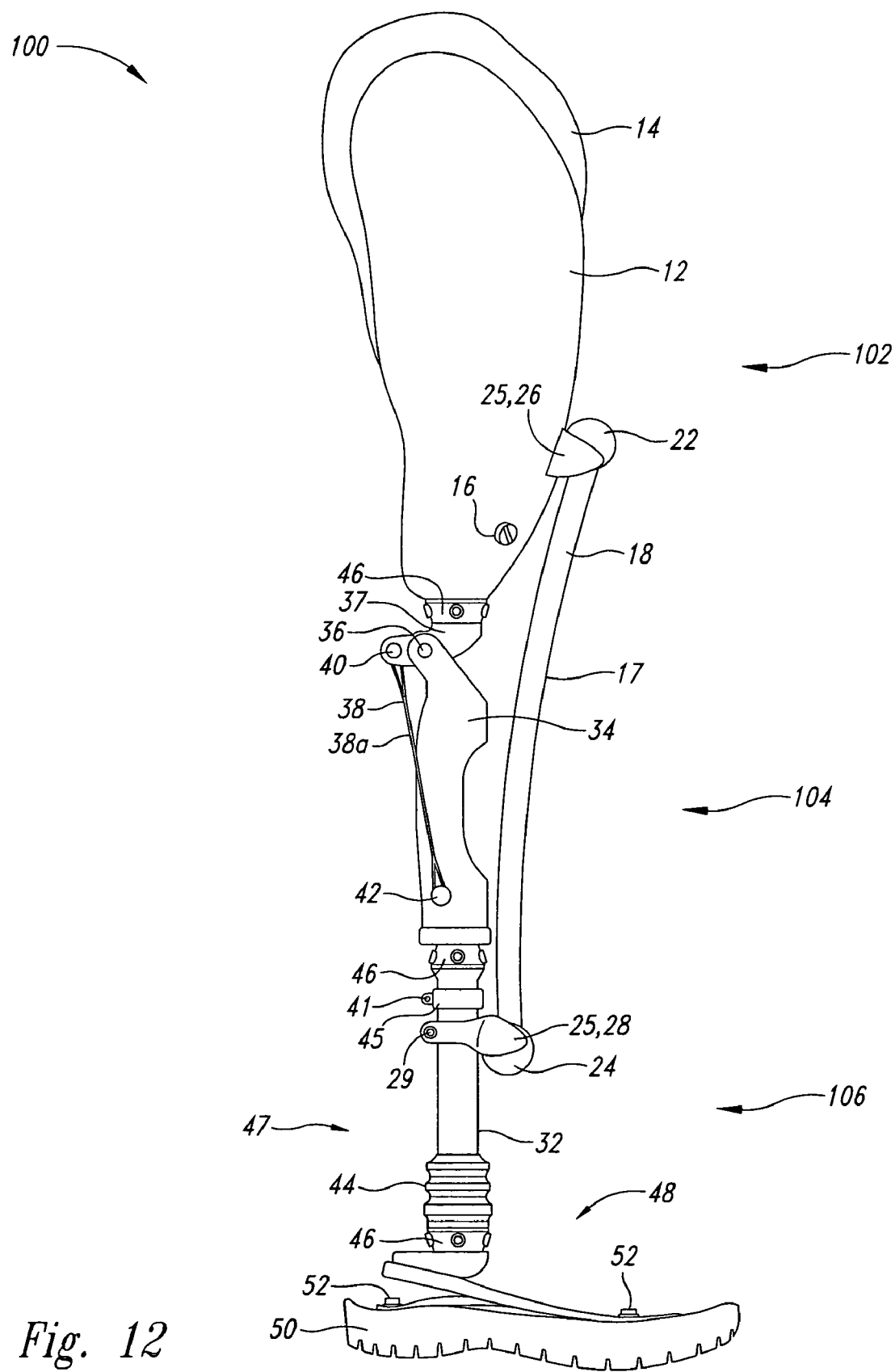
FIG. 12 is a right elevational view of an implementation of the prosthesis system depicted in FIG. 11.
Figure 13:
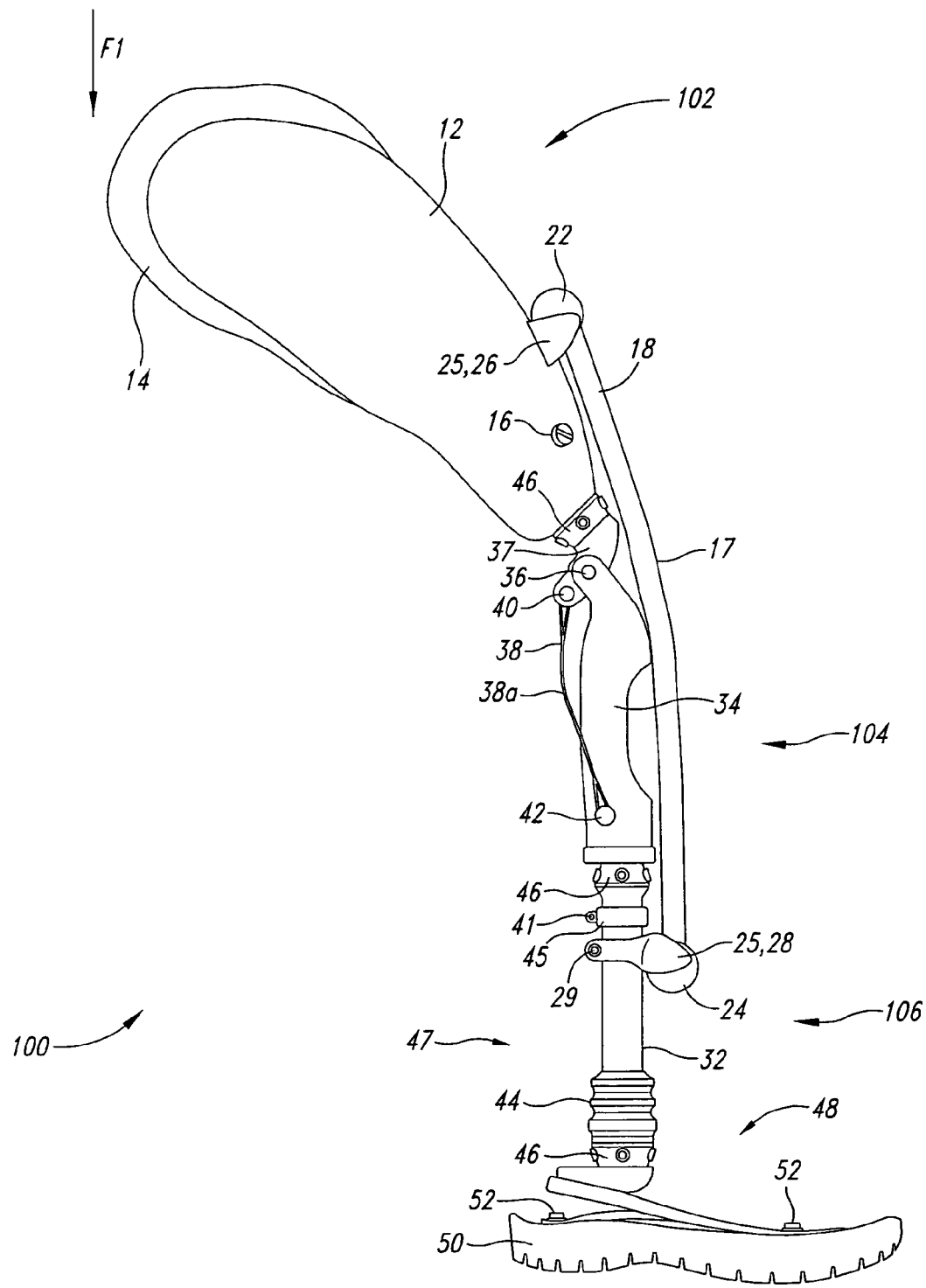
FIG. 13 a right elevational view of an implementation of the same prosthesis system depicted in FIG. 11, but alternately shown in a forty-five degree bent position.
Figure 14:
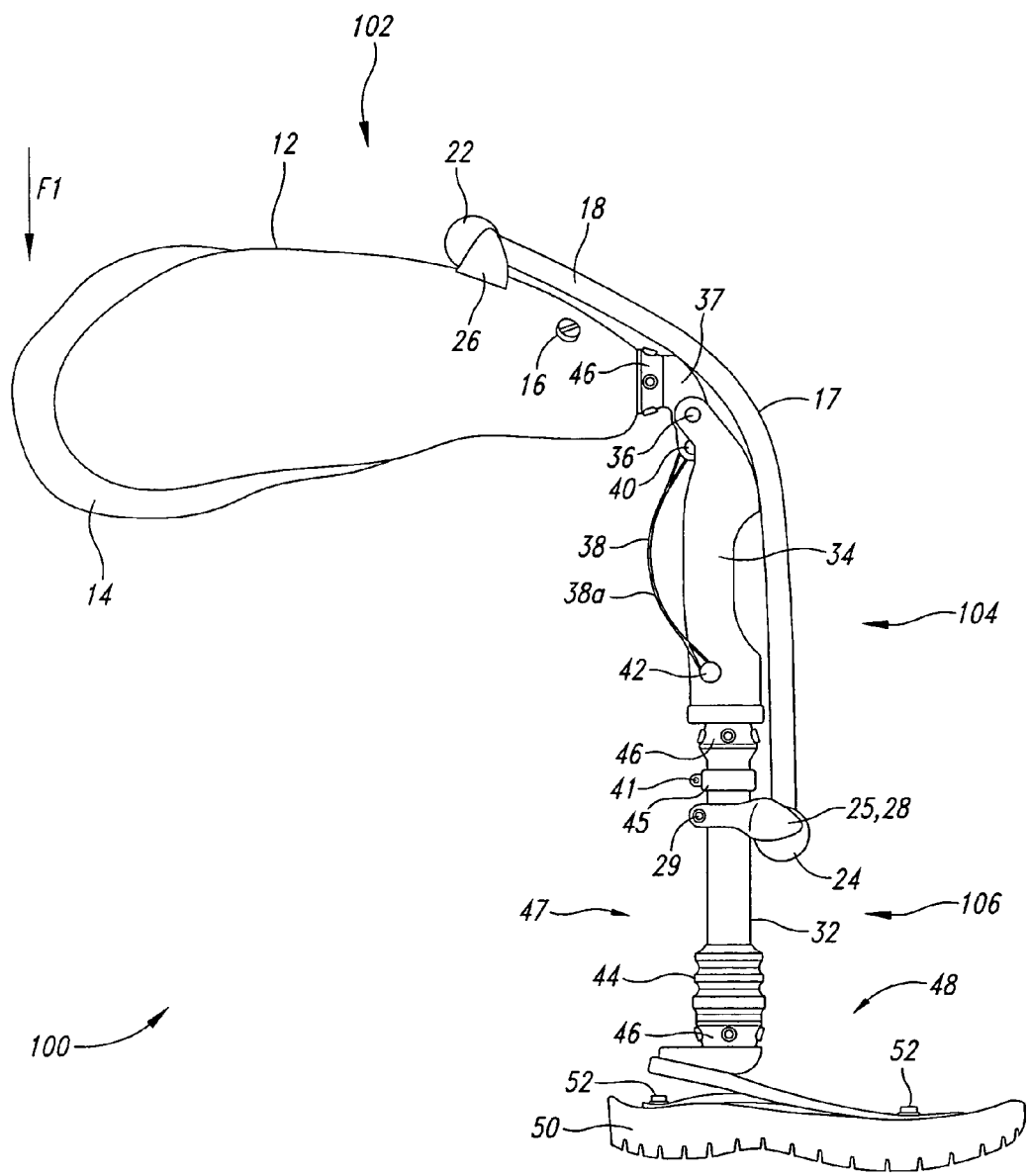
FIG. 14 is a right elevational view of an implementation the same prosthesis system depicted in FIG. 11, but alternately shown in a ninety degree bent position.

One elastic member 18 may be mounted to the lower portion 106 via a lower ball retainer 28, having the middle portion 17 routed frontally across the knee frame 34 of the joint portion 104, and mounted to the upper portion 102 via an upper ball retainer 26, such as shown in FIG. 11.

Figure 15:
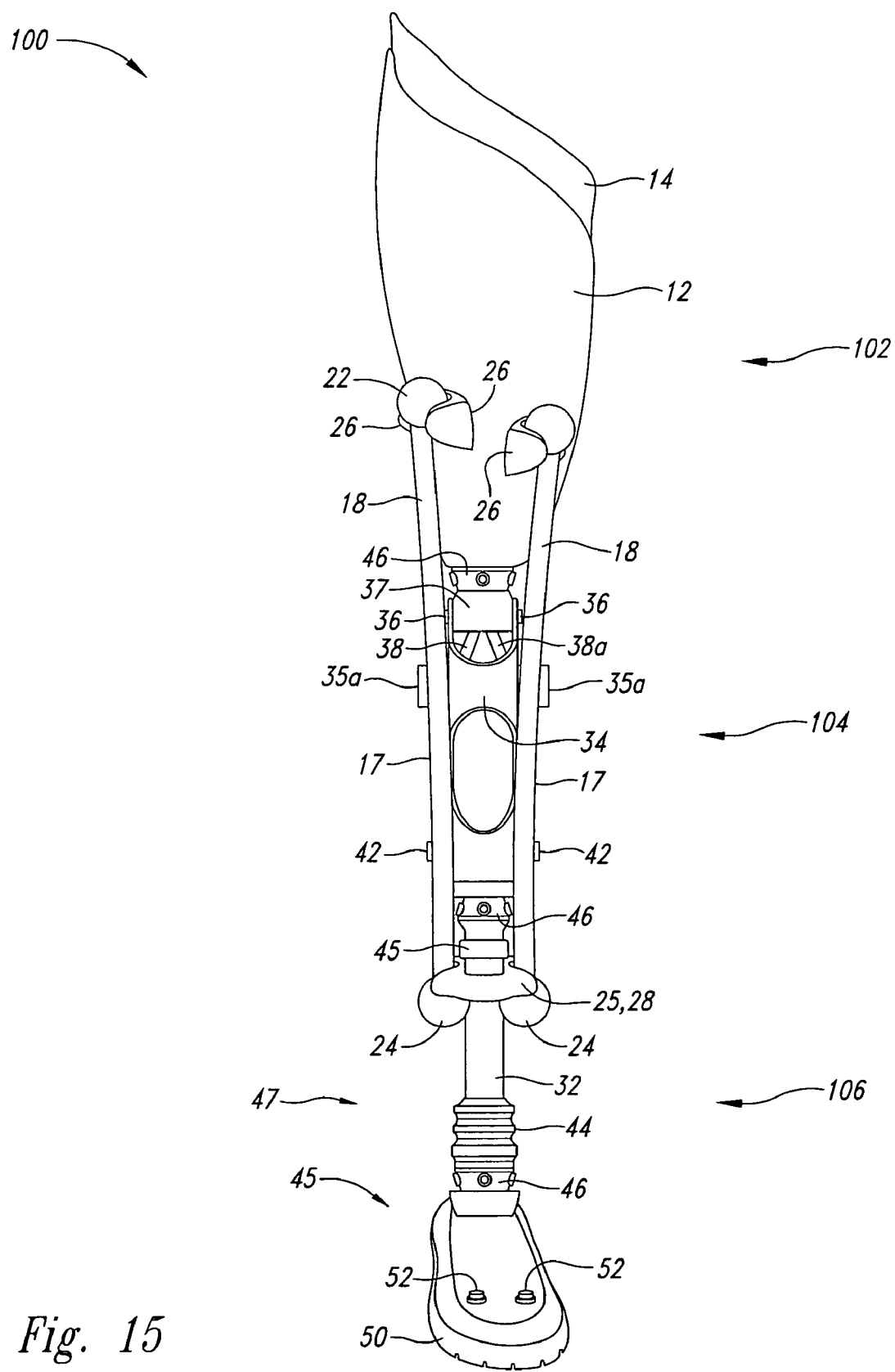
FIG. 15 is a front elevational view of an alternative implementation of a prosthesis system shown in the resting position, having two elastic members frontally routed.
Figure 17:
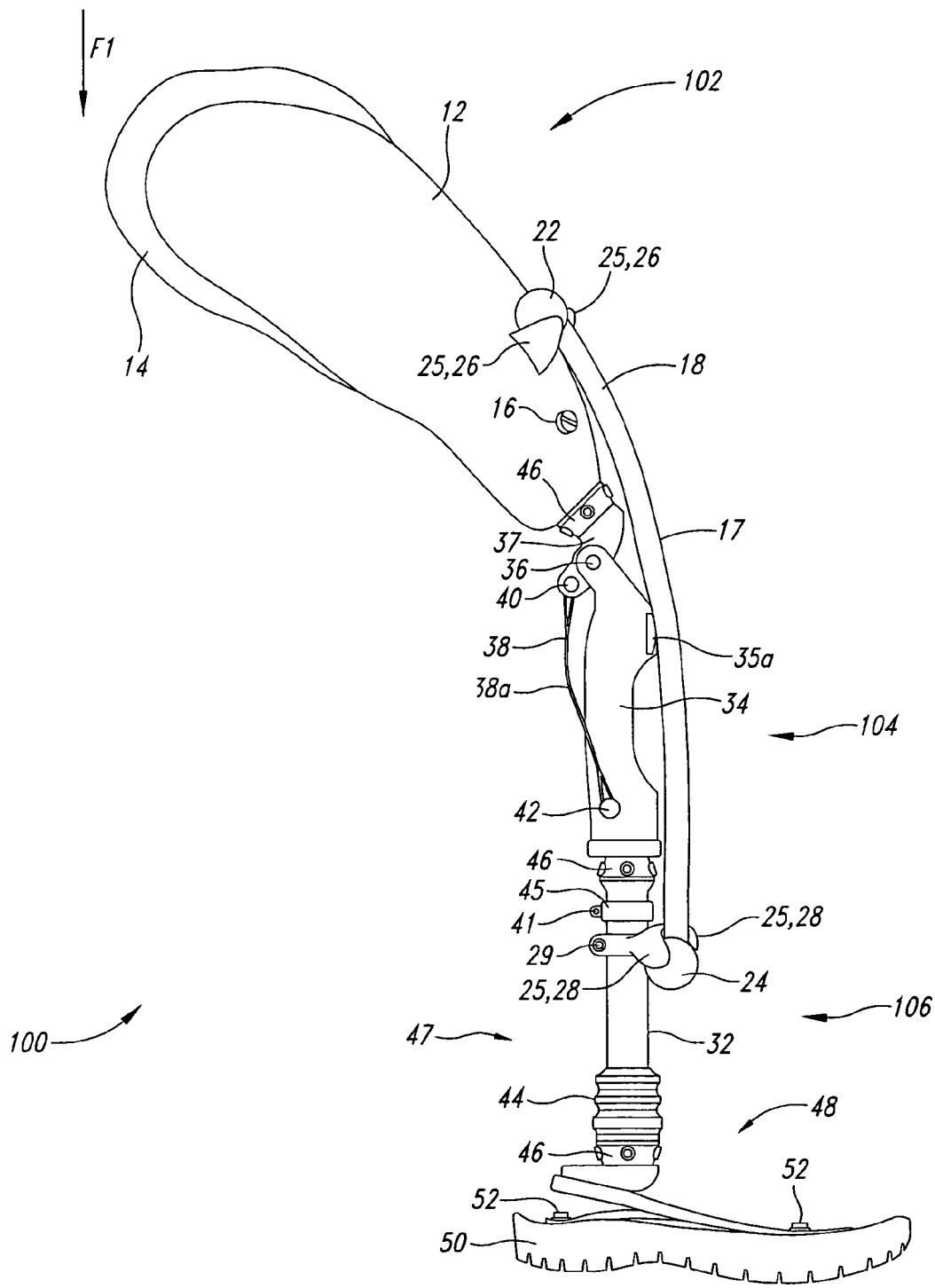
FIG. 17 is a right elevational view of an implementation of the same prosthesis system depicted in FIG. 15, but alternately shown in a forty-five degree bent position.
Figure 18:
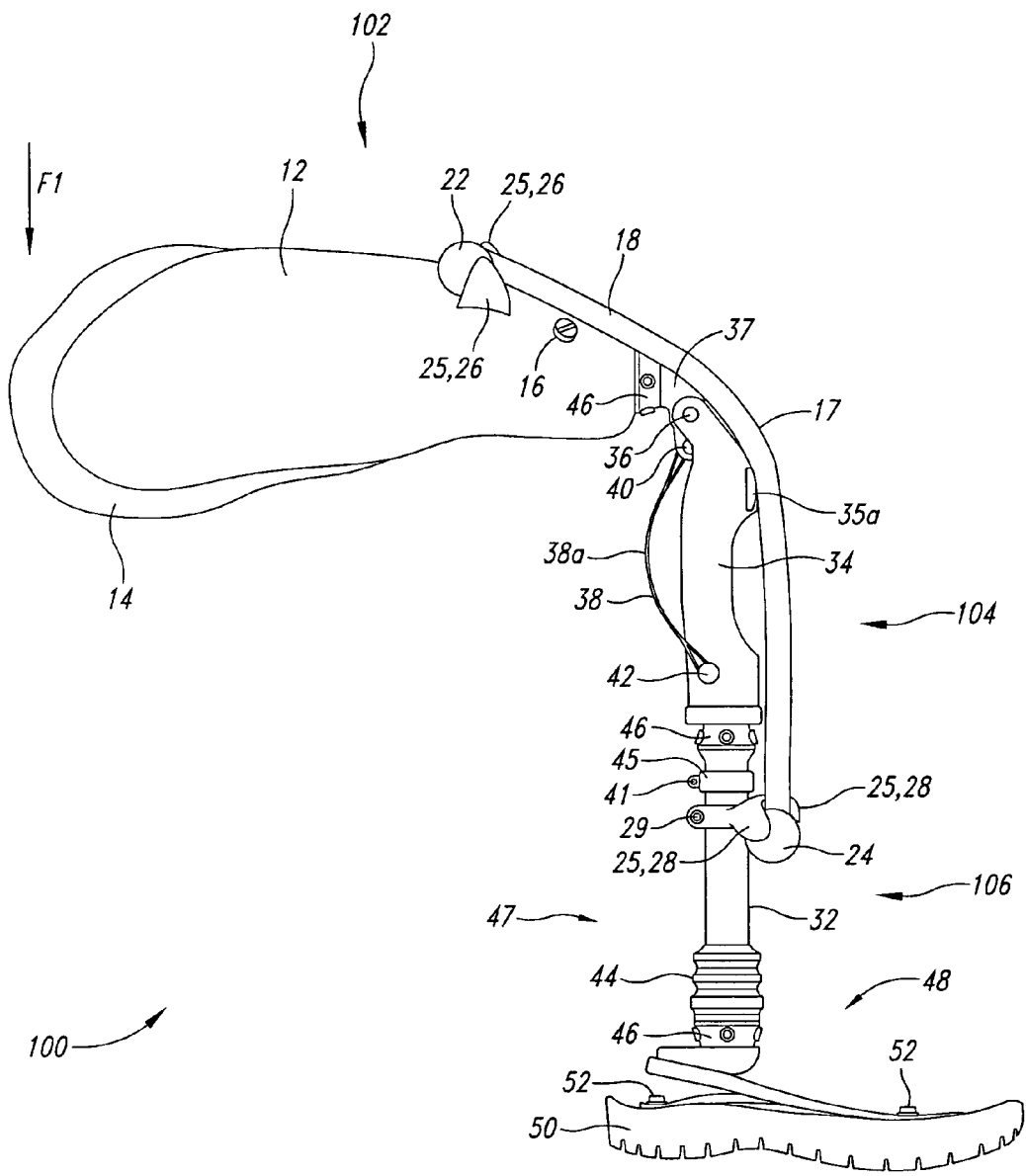
FIG. 18 is a right elevational view of an implementation of the same prosthesis system depicted in FIG. 15, but alternately shown in a ninety degree bent position.
Figure 19:
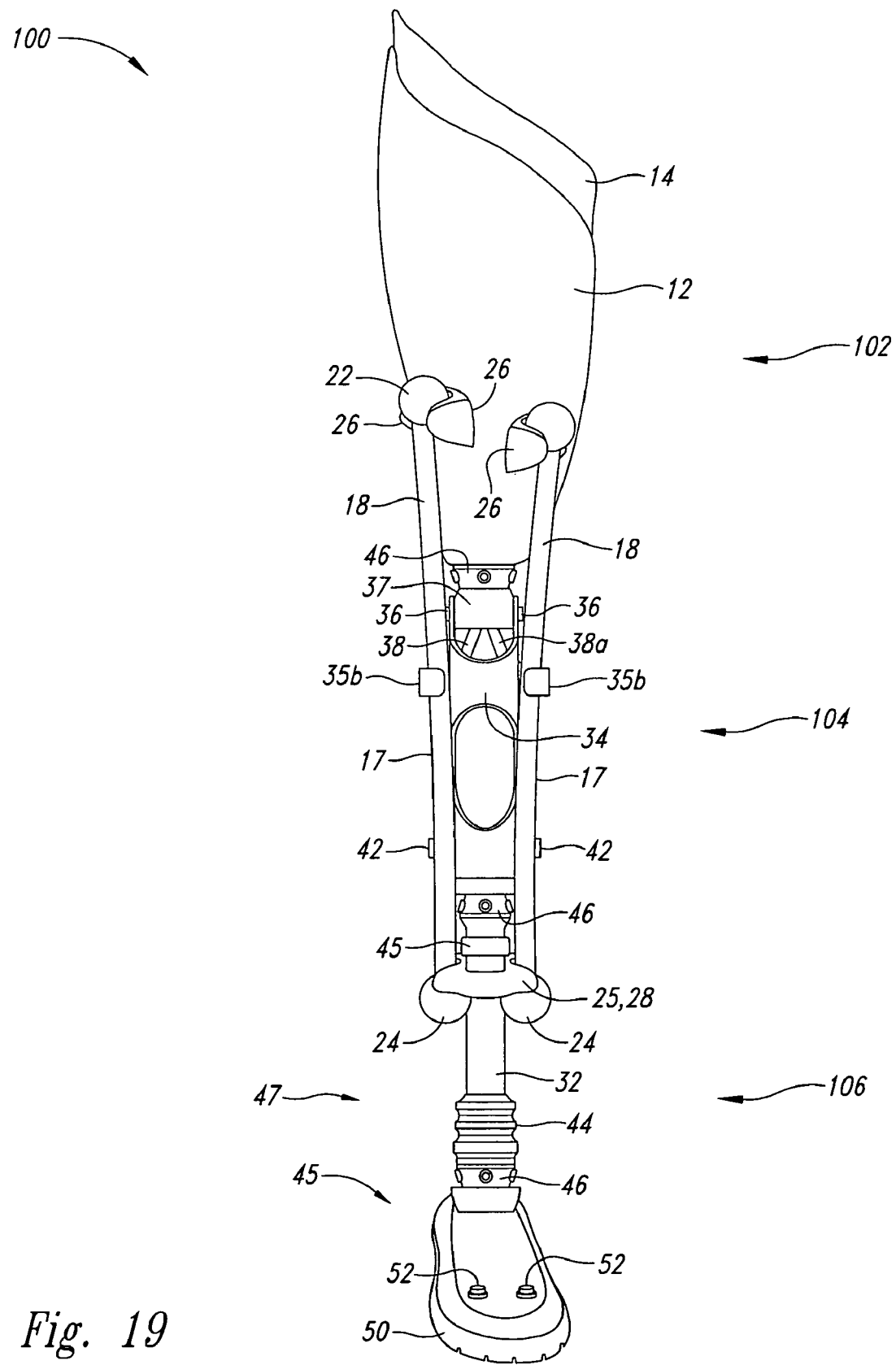
FIG. 19 is a front elevational view of an implementation of the same prosthesis system depicted in FIG. 15, but alternately shown with a hook style elastic member retainer.
Figure 20:
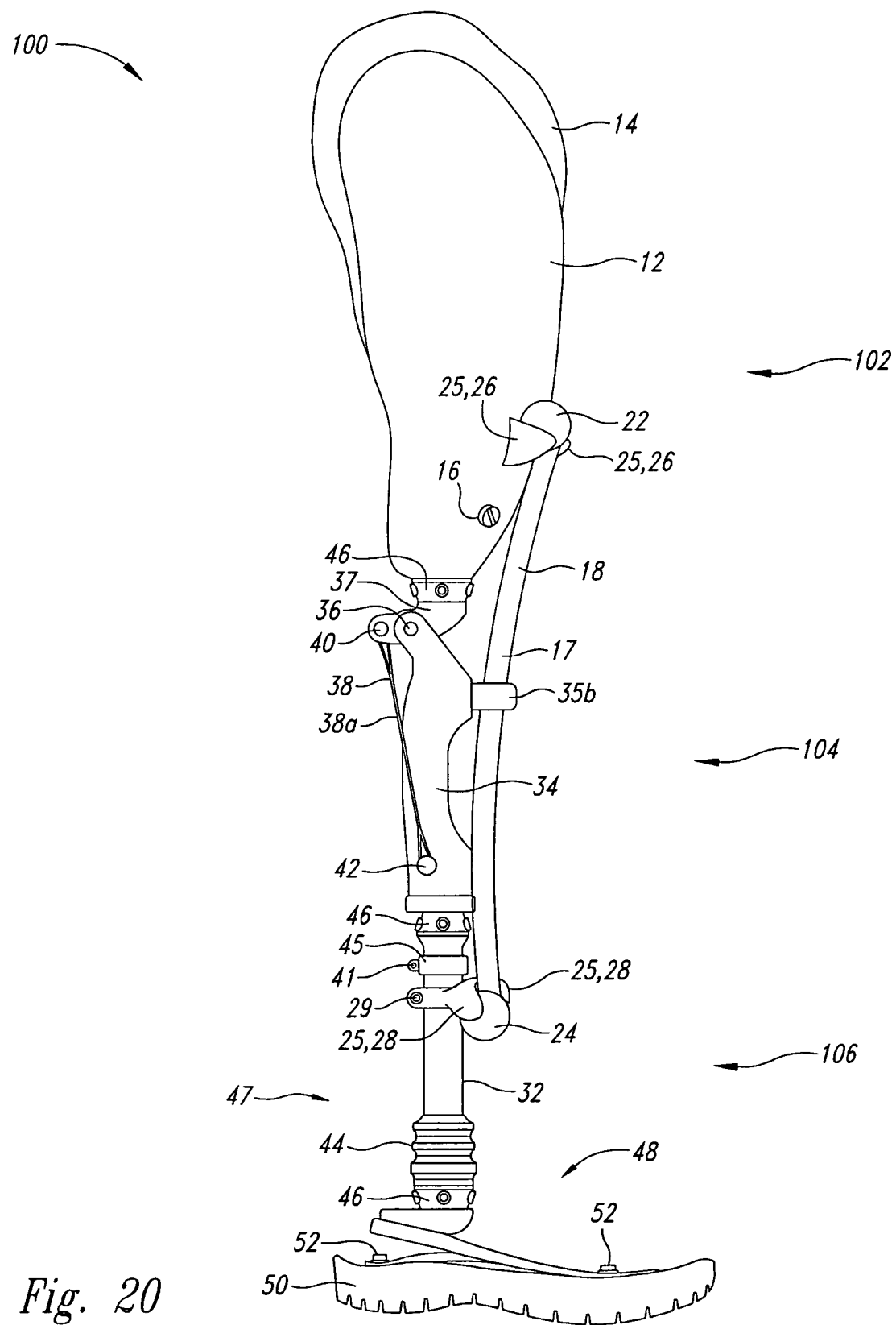
FIG. 20 is a right elevational view of an implementation of the same prosthesis system depicted in FIG. 20.

Two or more elastic members 18 may be mounted to the lower portion 106 via lower ball retainers 28, having the middle portions 17 routed frontally across the knee frame 34 of the joint portion 104, and mounted to the upper portion 102 via upper ball retainers 26, such as shown in FIG. 15. In this implementation it may be necessary to incorporate an elastic member retaining element 35 for supporting the middle portion 17 of the elastic member 18. The retaining element 35a may be configured as a simple seat, such as shown in FIGS. 15, 16, 17, and 18, or alternately configured as a hook type element 35b for a more secure retention of the middle portion 17, such as shown in FIGS. 19 and 20.

Figure 7:
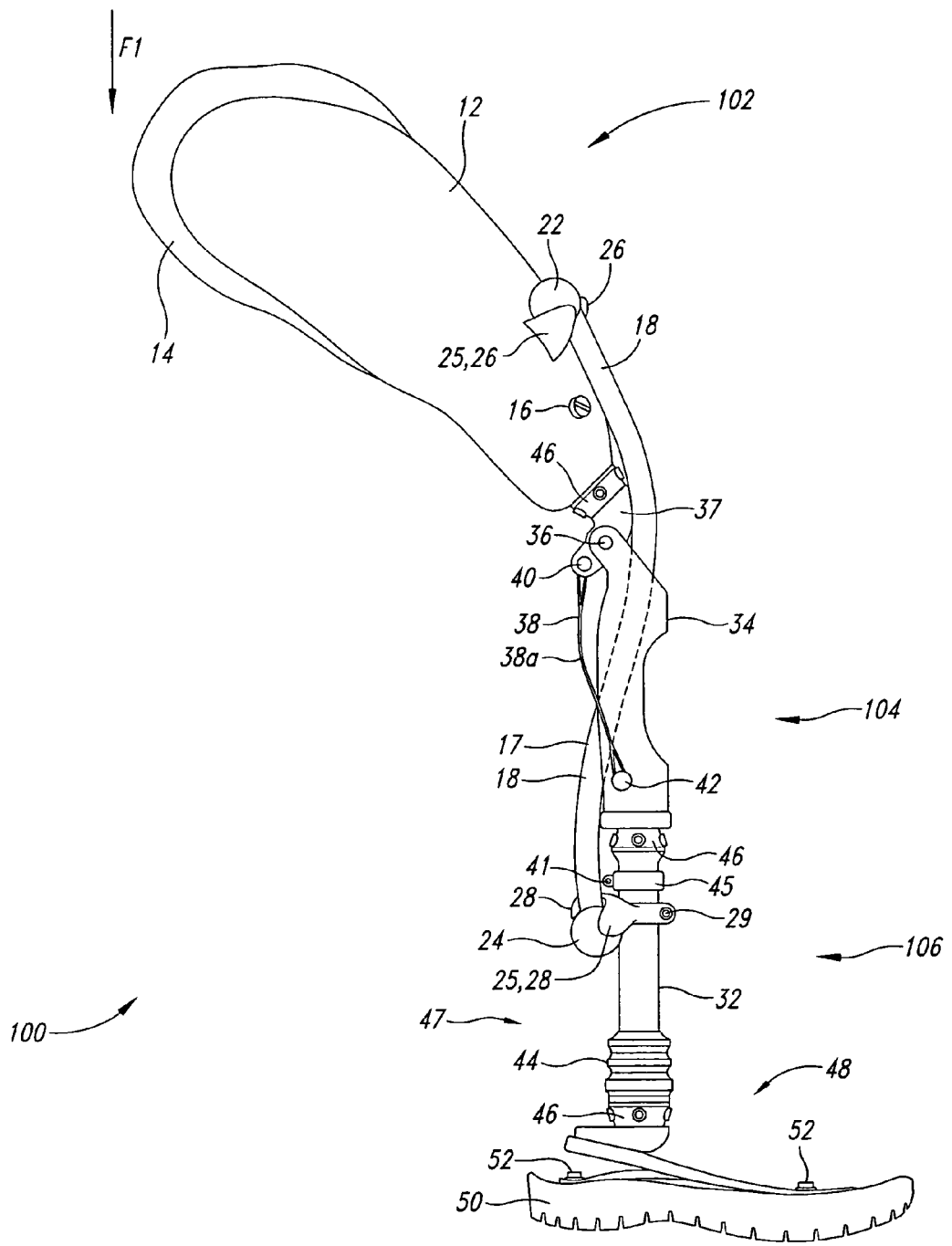
FIG. 7 is a right elevational view of an implementation of the same prosthesis system depicted in FIG. 1, but alternately shown in a forty-five degree bent position.
Figure 8:
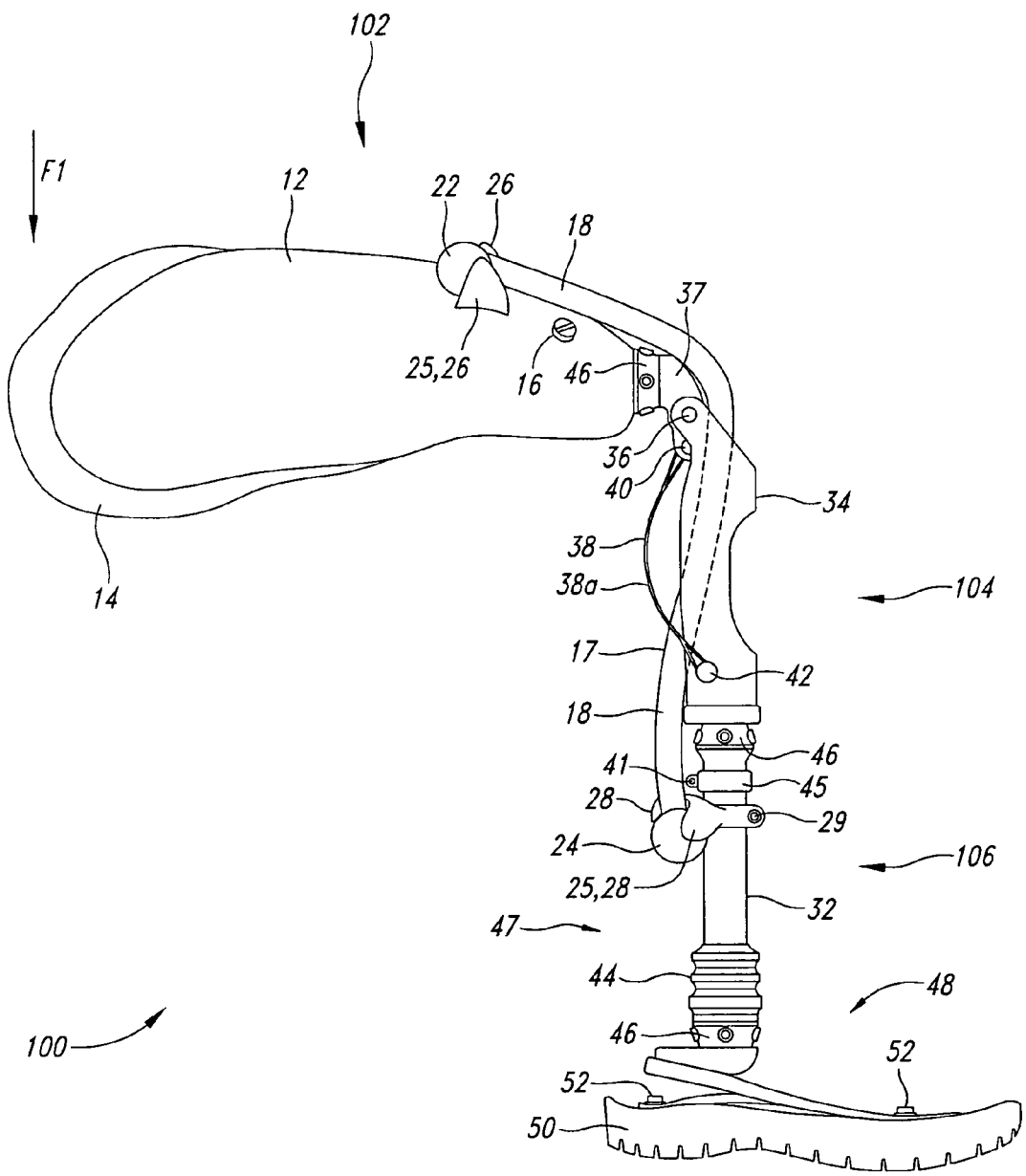
FIG. 8 is a right elevational view of an implementation of the same prosthesis system depicted in FIG. 1, but alternately shown in a ninety degree bent position.

By allowing the user to apply the force F1 of his or her own body weight, the system seeks a bent position. In other words, the upper portion 102 rotates around the knee fulcrum 36 and down towards the lower portion 106, as shown if FIGS. 7 and 8. This may in some respects mimic the bending of a knee. While in a bent position the elastic member(s) 18 are further stressed and applying a tensional force between the upper portion 102 and lower portion 106, such as shown in FIGS. 7 and 8. The tensional force applied by the elastic member(s) 18 will return the system to a resting position when the force F1 of the user's body weight is diminished or removed, such as shown in FIG. 6. In some respects this may mimic the function of the quadriceps muscles of the leg, acting as an extensor.

Figure 16:
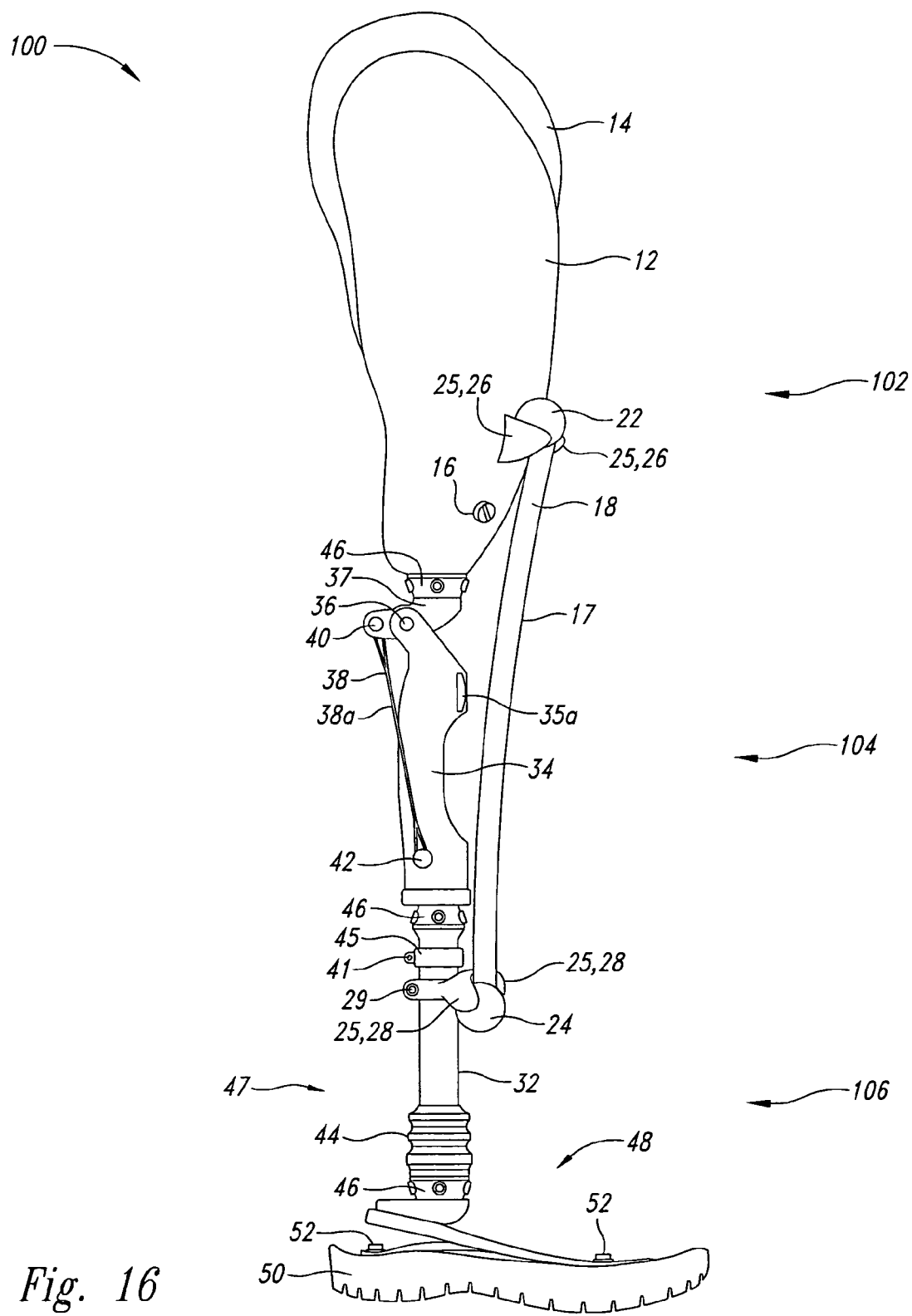
FIG. 16 is a right elevational view of an implementation of the prosthesis system depicted in FIG. 15, and shown with an adjustable strap acting as an anti-hyperextension member.
Figure 21:
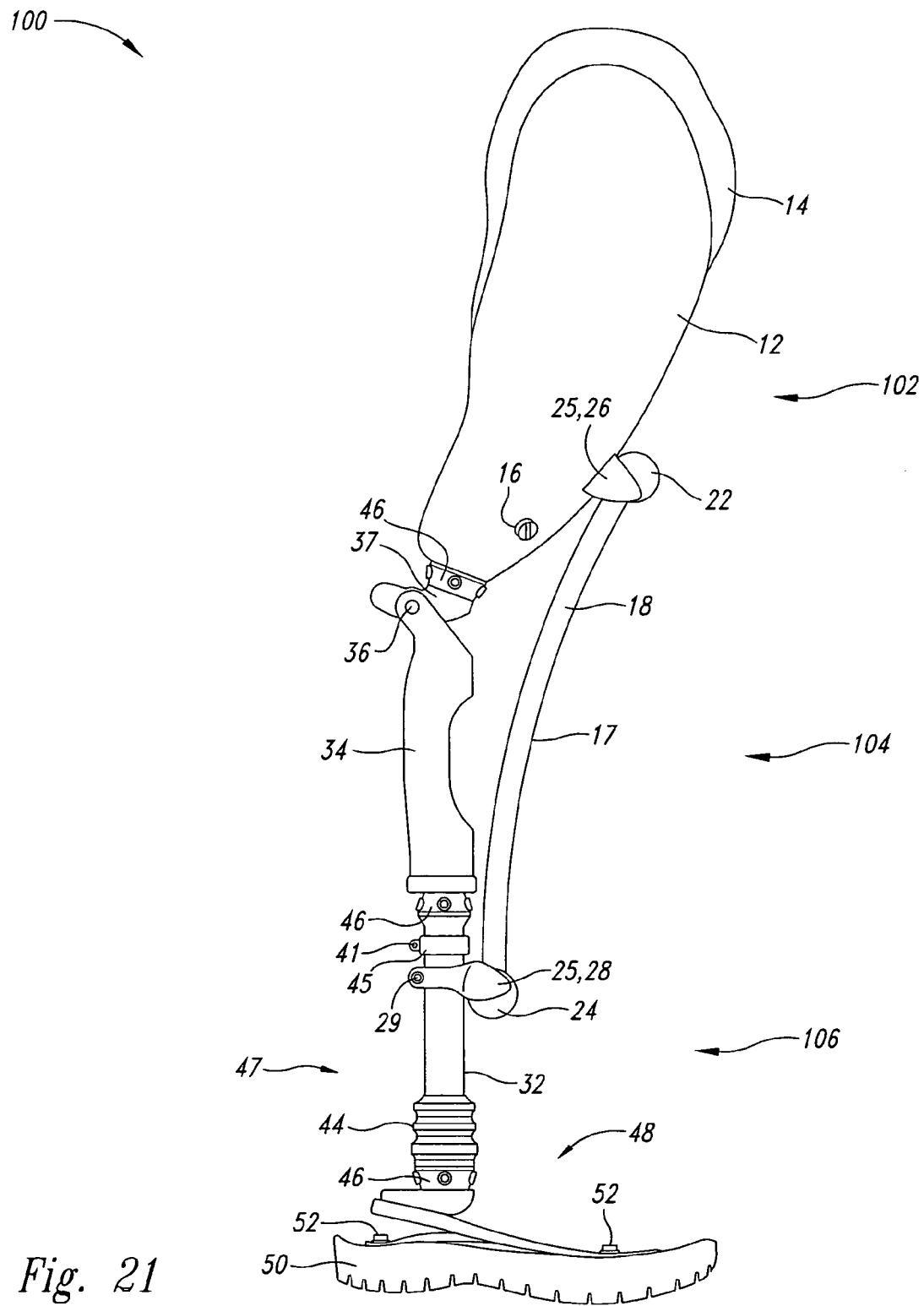
FIG. 21 is a right elevation view of a prosthesis system in a hyper extended state, and lacking an anti-hyperextension member.
Figure 22:
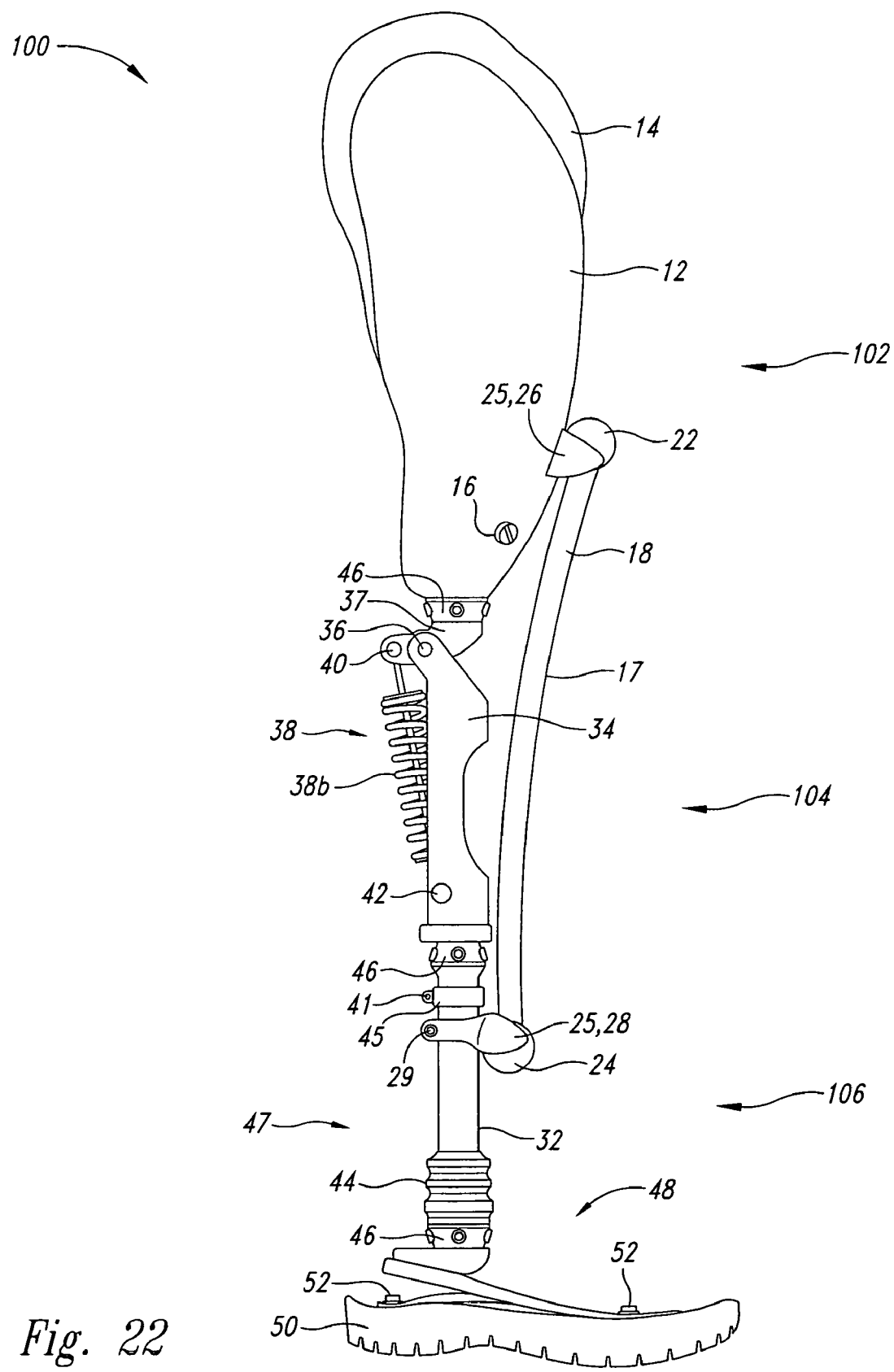
FIG. 22 is a right elevational view of an alternative implementation of the prosthesis system depicted in FIG. 15, but alternately shown with an adjustable tension spring acting as an anti-hyperextension member.
Figure 23:
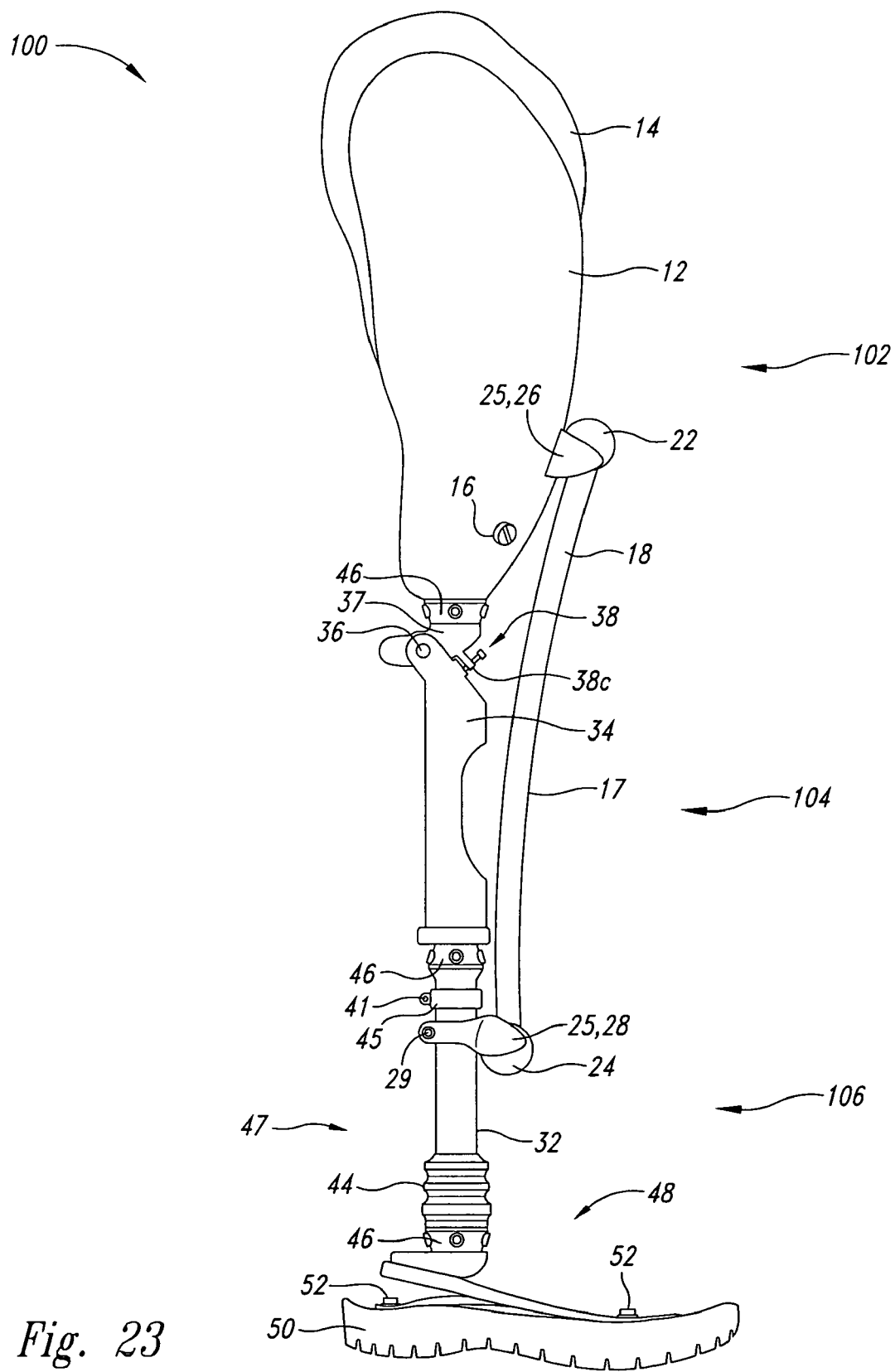
FIG. 23 is a right elevational view of an alternative implementation of the prosthesis system depicted in FIG. 15, but alternately shown with an adjustable stop acting as an anti-hyperextension member.
Figure 24:
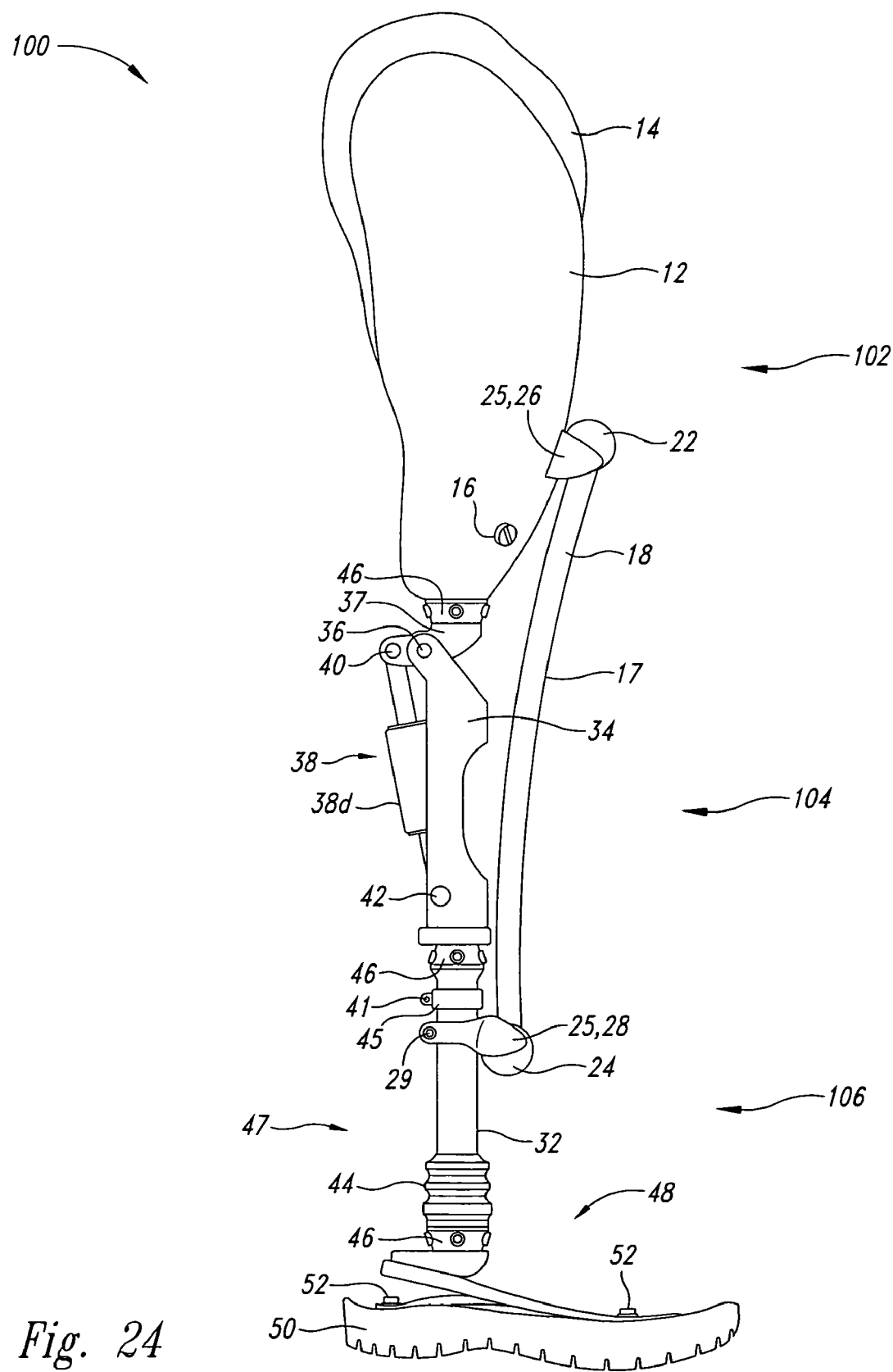
FIG. 24 is a right elevational view of an alternative implementation of the prosthesis system depicted in FIG. 15, but alternately shown with a fluidic shock absorber acting as an anti-hyperextension member.

The tensional force applied by the elastic member(s) can cause the system 100 to hyperextend beyond the resting position, such as shown in FIG. 21. To prevent hyperextension, an adjustable anti-hyperextension member 38 may be integrated into the system 100. This can be mounted between an upper attachment point 40 and a lower attachment point 42 within the joint portion 104. The anti-hyperextension member 38 can also be adjusted so as to define the resting position of the system 100. A simple strap 38a made of a resilient or non-resilient material could be used as the acting anti-extension member 38, such as shown in FIGS. 16, 17, and 18, and could further include examples such as: an adjustable tension spring 38b such as shown in FIG. 22, an adjustable stop 38c such as shown in FIG. 23, and/or an adjustable fluidic shock absorber 38d such as shown in FIG. 24.

The ankle segment 47 may encompass a pyramid adapter 46 and/or a resilient ankle joint 44. The resilient ankle joint, allowing a three-dimensional movement of the foot 48 relative to the lower portion 106, will deter any torsional and/or lateral forces being transferred from the foot to the user. This can help alleviate stress on the user's body, and may reduce the potential for injury to the user.

Figure 25:
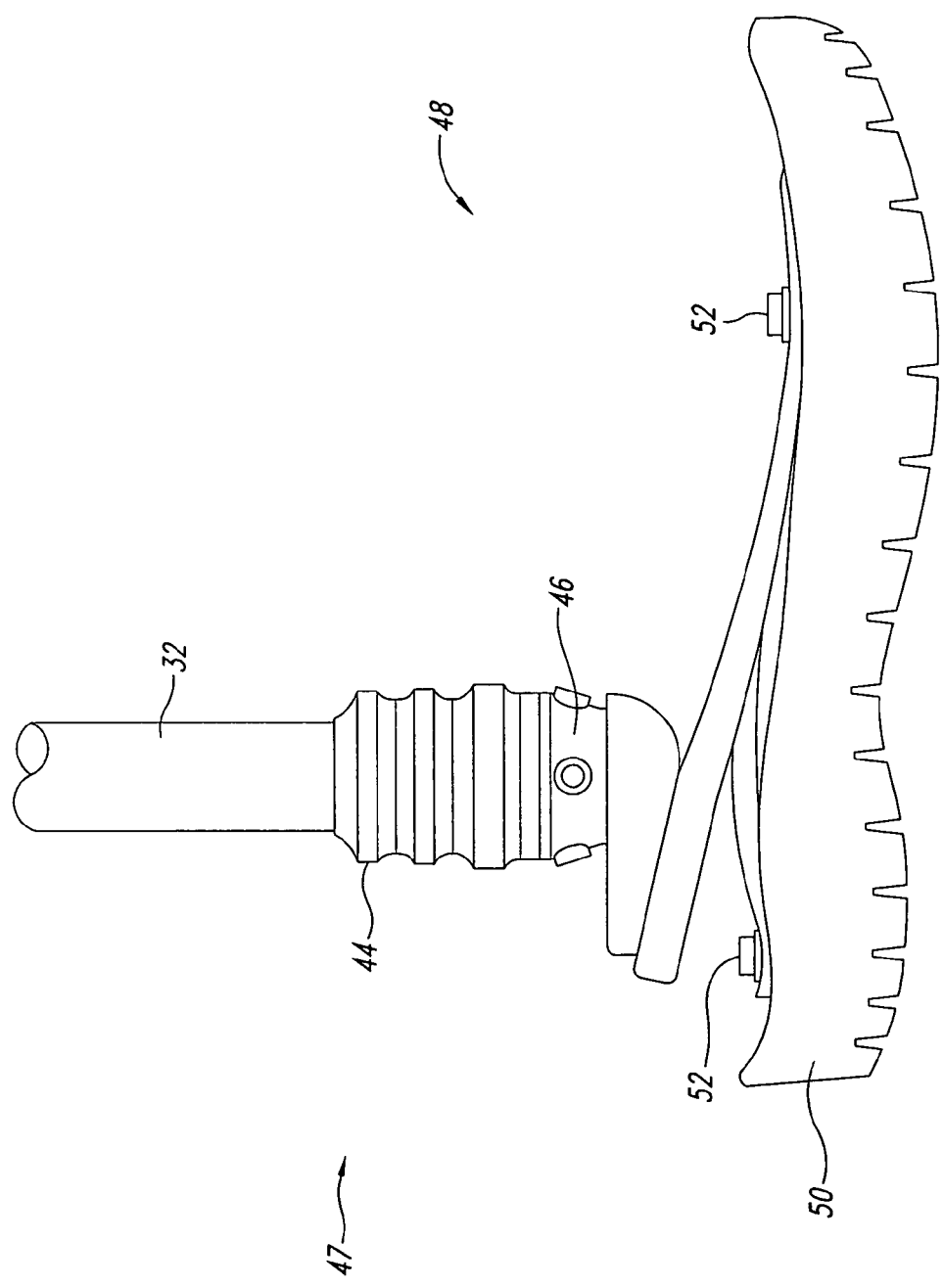
FIG. 25 is a right elevational view of an implementation of the foot portion having a standard shoe.
Figure 26:
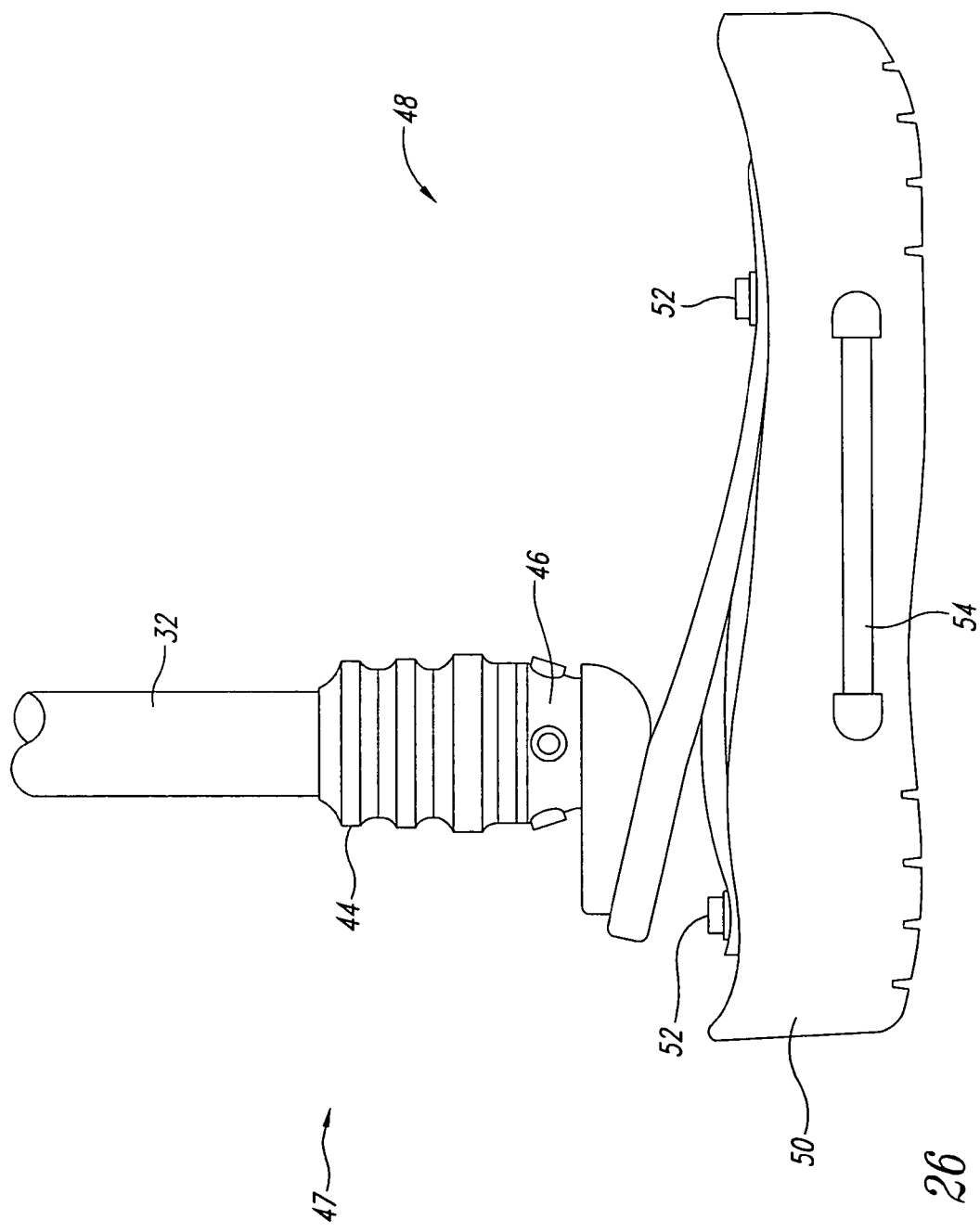
FIG. 26 is a right elevational view of an alternative implementation of the foot portion having a clip-in style snowboard and/or wakeboard shoe.
Figure 27:
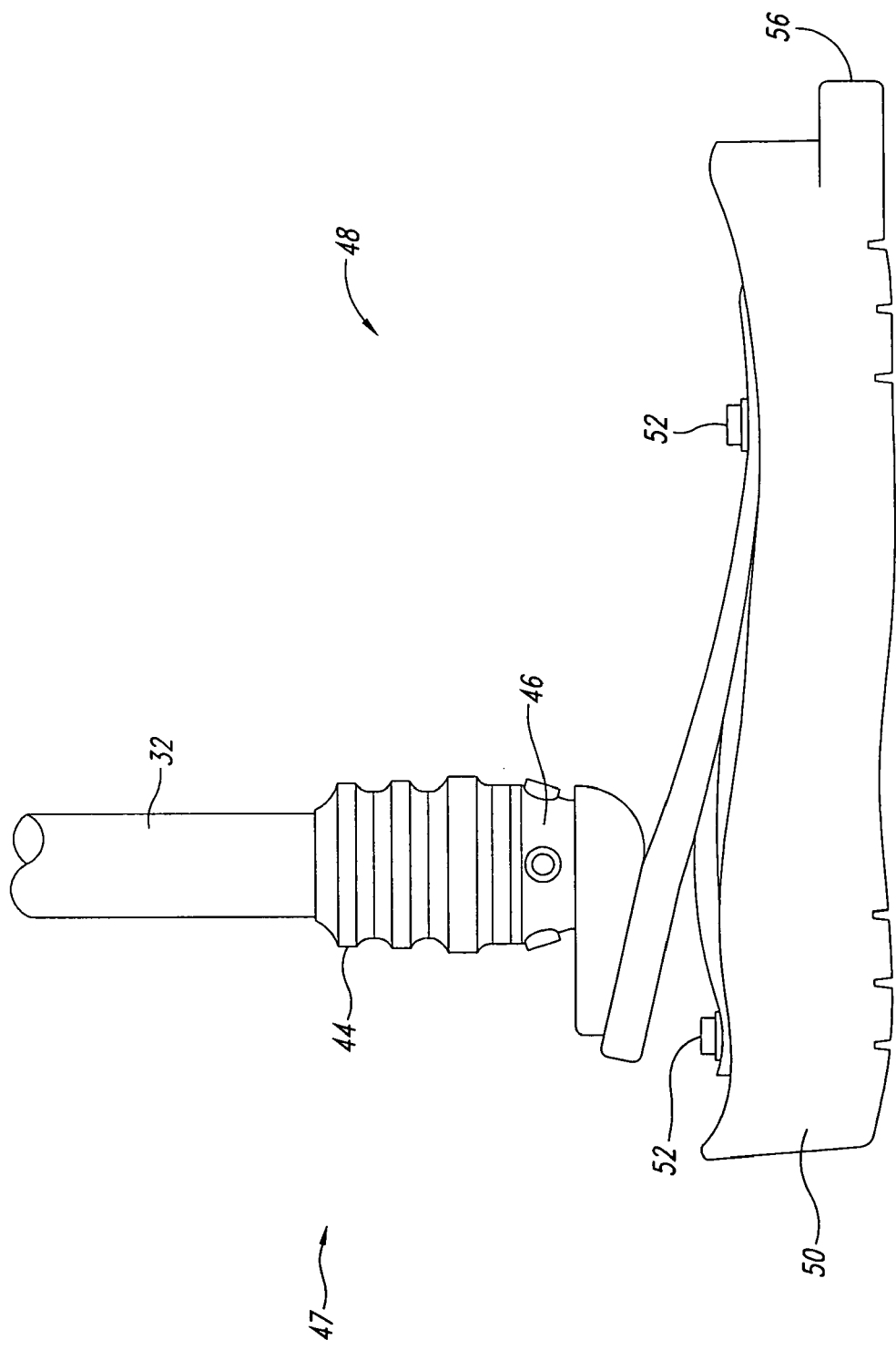
FIG. 27 is a right elevational view of an alternative implementation of the foot portion having a cross-country and/or telemarking shoe.
Figure 28:
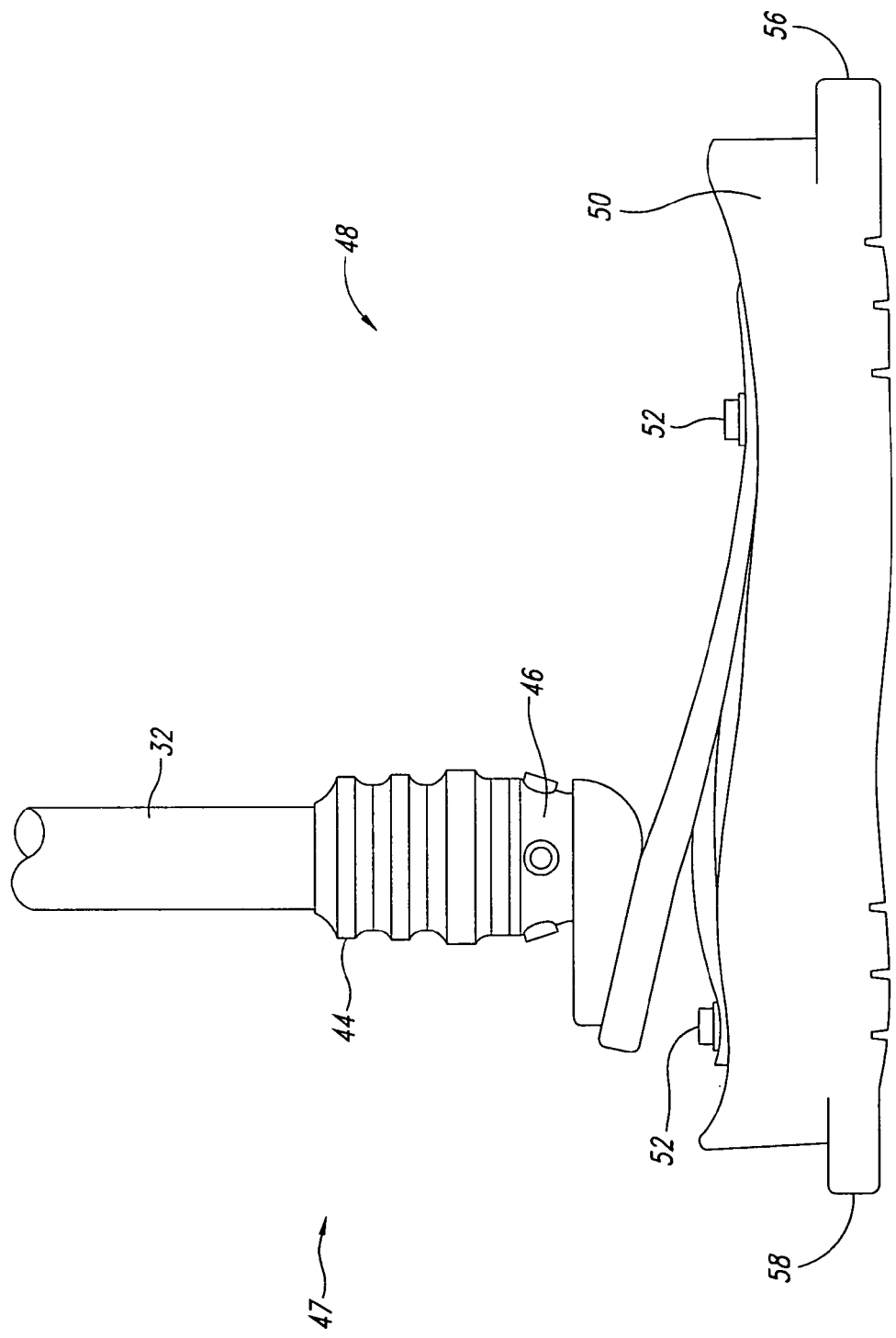
FIG. 28 is a right elevational view of an alternative implementation of the foot portion having a downhill snow ski shoe.
Figure 29:
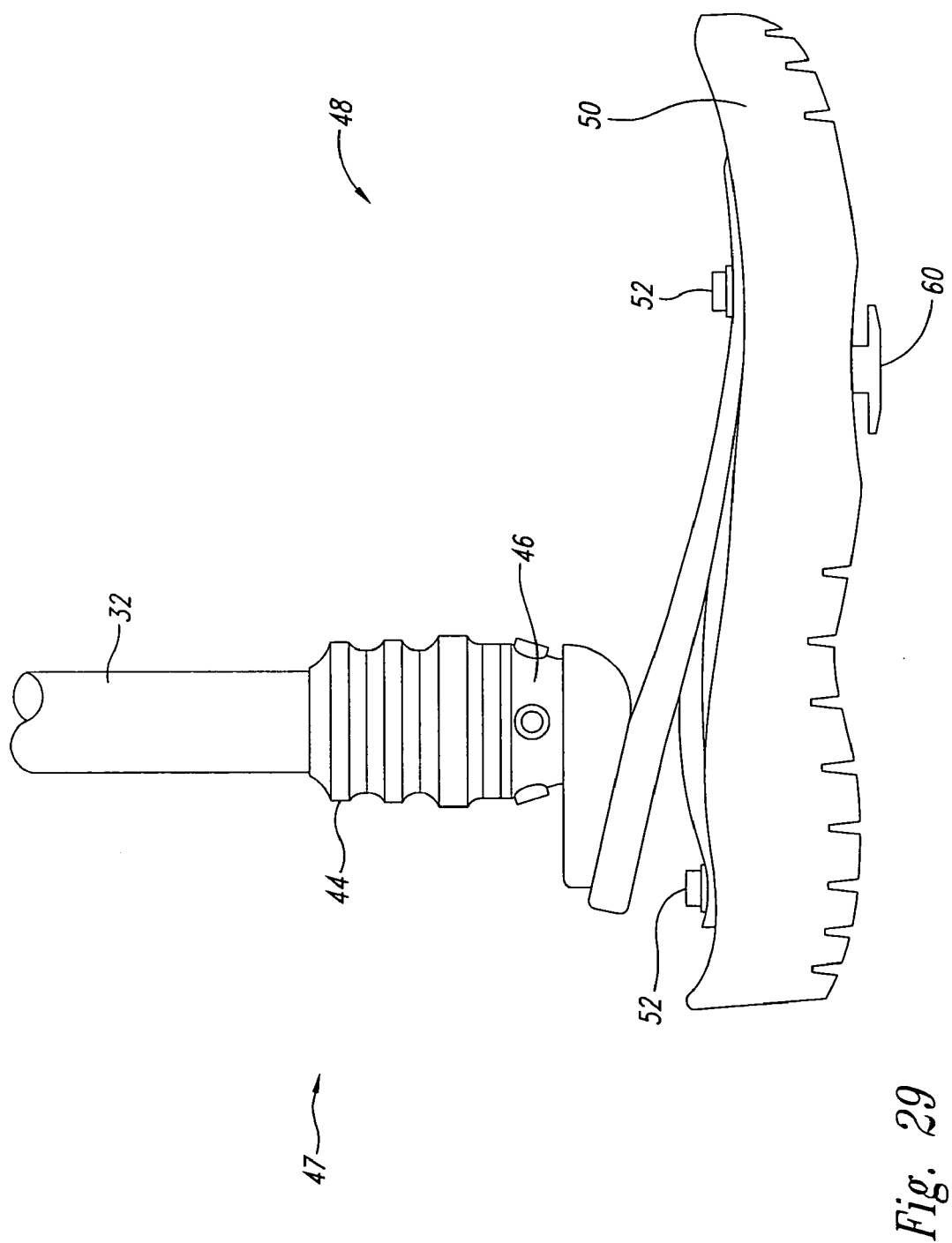
FIG. 29 is a right elevational view of an alternative implementation of the foot portion having a bicycle clipless type shoe.
Figure 30:
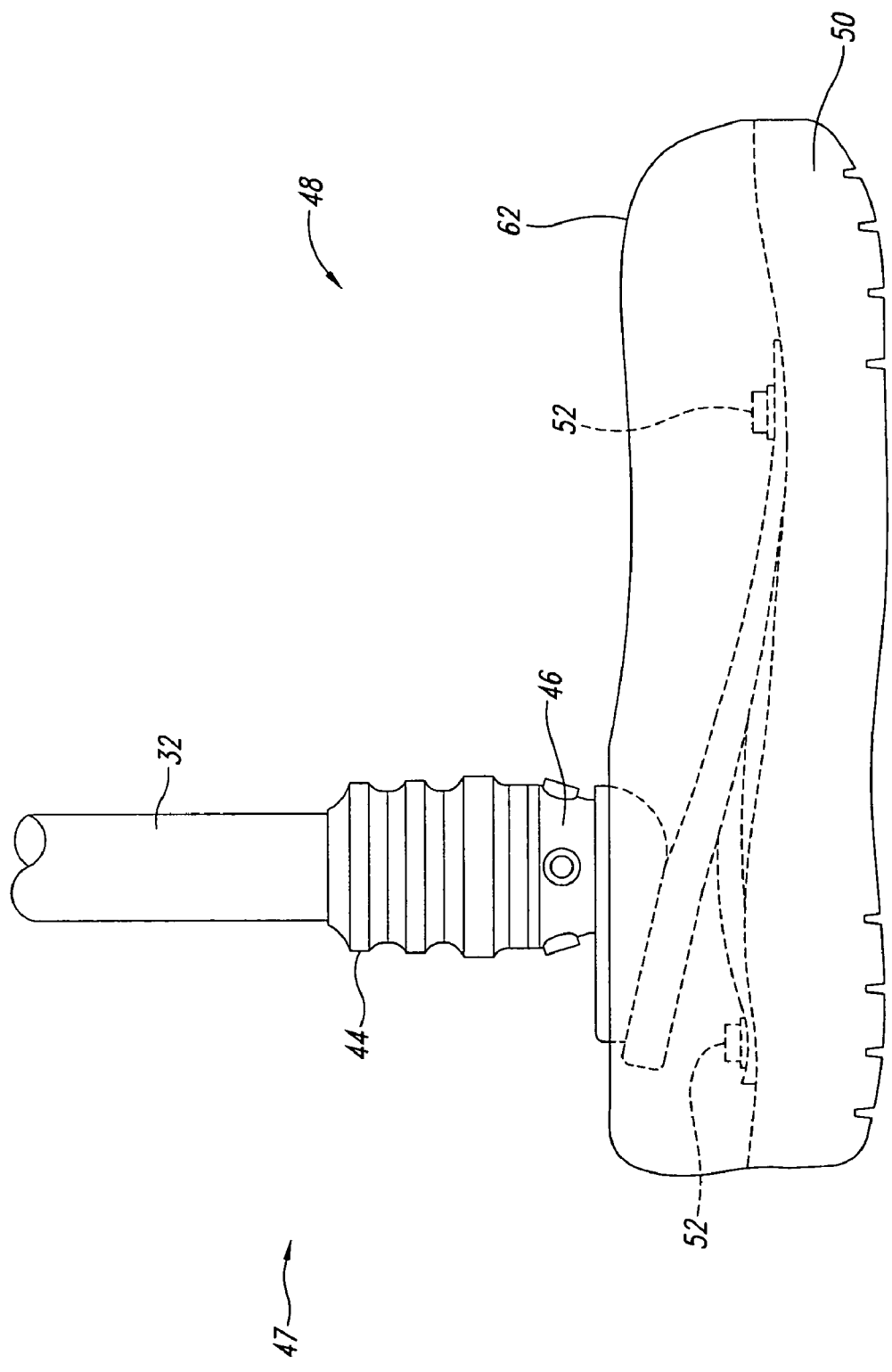
FIG. 30 is a right elevational view of an alternative implementation of the foot portion having a full upper shoe, for use in snowboard bindings, bicycle toe cages, snowshoes, crampons, water ski bindings, and/or other slip-in type bindings.

The foot 48 may be comprised of a shoe 50 and/or any number of shoe fastener(s) 52. Additionally, the shoe 50 may be removed from the foot 48 via the fastener(s) 52, providing the ability to change the shoe in order to suit any number of various activities. The shoe 50 can vary in form and function, examples include: a standard shoe sole such as shown in FIG. 25, a snowboarding or wakeboarding clip-in shoe with lateral clip bars 54 such as shown in FIG. 26, a cross country ski shoe with a toe clip 56 such as shown in FIG. 27, a downhill snow ski shoe with a toe clip 56 and heel clip 58 such as shown in FIG. 28, a bicycling shoe with a clipless system 60 such as shown in FIG. 29, and/or a shoe having a full upper portion 62 for use in various strap-in bindings such, as shown in FIG. 30.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A prosthesis system for a human leg comprising:
an upper portion configured for coupling with the human leg;
a lower portion configured for coupling with an appendage;
a joint portion, the upper portion hingedly coupled to the lower portion via the joint portion such that the lower portion and the upper portion are pivotally movable with respect to one another between an extended state and a bent state; and
an elongated elastic cord member comprising an elastic middle portion between first and second end retaining portions of a harder material than the elastic middle portion, the first end retaining portion coupled to a first retainer positioned on the upper portion and the second end retaining portion coupled to a second retainer positioned on the lower portion, wherein at least one of the first and second end retaining portions further comprises a part-spherical retaining ball, and at least one retaining element further comprises a ball retainer that is shaped to accept the corresponding part-spherical retaining ball end portion of the elastic cord member.

2. The system of claim 1 wherein the first retainer having the first end retaining portion of the elongated elastic cord coupled thereto is frontally located on the upper portion, and the second retainer having the second end retaining portion of the elongated elastic cord coupled thereto is frontally located on the lower portion, and the elastic cord member being secured by tension thereof between the first and second retainers.

3. The system of claim 1 wherein the first and second end retaining portions of the elastic cord member are further coupled to the elastic middle portion therebetween.

4. The system of claim 1 wherein the first portion of the elongated elastic cord is frontally located on the upper portion and the second portion of the elongated elastic cord is rearwardly located on the lower portion.

5. The system of claim 1 wherein the first end retaining portion of the elongated elastic cord further comprises a first ball comprised of the harder material, and the first retainer being shaped to receive the first ball; and
the second end portion of the elongated elastic cord further comprises a second ball comprised of the harder material, and the second retainer being shaped to receive the second ball.

6. The system of claim 5 further including an anti-hyperextension member rearwardly coupled to the upper portion and rearwardly coupled to the lower portion.

7. The system of claim 6 wherein the anti-hyperextension member is a strap.

8. The system of claim 6 wherein the anti-hyperextension member is a spring.

9. The system of claim 6 wherein the anti-hyperextension member is a shock absorber.

10. The system of claim 5 wherein the lower portion is configured for coupling with one of the following as the appendage: a wakeboard shoe, a clipless bicycle shoe, a telemarking shoe, and a snow ski boot.

11. The system of claim 1 wherein each of the first and second end retaining portions further comprises a part-spherical retaining ball coupled to the elastic middle portion therebetween; and
each retaining element is further shaped to accept the corresponding part-spherical retaining ball end portion of the elastic cord member, the retaining ball end portion being secured in the retaining element by tension of the elastic cord member.

12. A prosthesis system for a human leg comprising:
an upper portion configured for coupling with the human leg;
a lower portion configured for coupling with a shoe, the lower portion further comprising a knee frame;
a joint portion, the upper portion hingedly coupled to the lower portion via the joint portion such that the lower portion and the upper portion are pivotally movable with respect to one another between an extended position and a bent position; and
an elongated elastic cord member comprising a first portion coupled to the upper portion and a second portion coupled to the lower portion, the elastic cord member comprising an overall length between the first portion and the second portion in the extended position shorter than an overall length in the bent position, and wherein the elongated elastic cord is routed through the knee frame from a frontal location on the upper portion to a rearward location on the lower portion.

13. A prosthesis system for a human leg comprising:
an upper portion configured for coupling with the human leg, the upper portion further comprising a plurality of first retaining elements;
a lower portion, the upper portion further comprising a plurality of second retaining elements;
a joint portion, the upper portion hingedly coupled to the lower portion via the joint portion such that the lower portion and the upper portion are pivotally movable with respect to one another between an extended state and a bent state; and
a plurality of elongated elastic members each comprising an elastic middle portion between first and second end retaining portions of relatively harder material, each of the first end retaining portions coupled to one of the plurality of first retaining elements of the upper portion and each of the second end retaining portions coupled to one of the plurality of second retaining elements of the lower portion and tension in the elastic middle portion securing the first and second end retaining portions relative to the respective first and second retaining elements, each of the elongated elastic members having a first length between the first portion and the second retaining portions in the extended state and a second length between the first retaining portion and the second retaining portion in the bent state, the first length being shorter than the second length.

14. The system of claim 13 wherein each of the plurality of first retaining elements is further frontally located on the upper portion, and one or more of the plurality of second retaining elements is further frontally located on the lower portion.

15. The system of claim 13 wherein the first and second end portions of each of the elongated elastic members further comprises a retaining ball; and
   each of the first and second retaining elements further comprises a ball retainer.

16. The system of claim 15 wherein each of the first and second retaining elements is further shaped to slidably engage with a respective one of the first and second end retaining portions of the elongated elastic members.

17. The system of claim 13 wherein each of the first retaining elements having the first end portion of one of the elongated elastic members coupled thereto is further frontally located on the upper portion, and each of the second retaining elements having the second end portion of one of the elongated elastic members coupled thereto is further rearwardly located on the lower portion.

18. The system of claim 17 wherein the lower portion further comprises a knee frame, and one or more of the elongated elastic members is routed through the knee frame from a different one of the first retaining elements frontally located on the upper portion to a different one of the second retaining elements rearwardly located on the lower portion.

* * * * *